US012318208B2

(12) United States Patent
Schram

(10) Patent No.: US 12,318,208 B2
(45) Date of Patent: Jun. 3, 2025

(54) TWO-LEAD QT INTERVAL PREDICTION

(71) Applicant: AliveCor, Inc., Mountain View, CA (US)

(72) Inventor: Matthew Schram, San Francisco, CA (US)

(73) Assignee: ALIVECOR, INC., Mountain View, CA (US)

( * ) Notice: Subject to any disclaimer, the term of this patent is extended or adjusted under 35 U.S.C. 154(b) by 146 days.

(21) Appl. No.: 17/357,701

(22) Filed: Jun. 24, 2021

(65) Prior Publication Data

US 2021/0401349 A1    Dec. 30, 2021

Related U.S. Application Data

(60) Provisional application No. 63/044,882, filed on Jun. 26, 2020.

(51) Int. Cl.
*A61B 5/36* (2021.01)
*A61B 5/00* (2006.01)
*A61B 5/271* (2021.01)

(52) U.S. Cl.
CPC .............. *A61B 5/36* (2021.01); *A61B 5/0006* (2013.01); *A61B 5/271* (2021.01); *A61B 2560/02* (2013.01)

(58) Field of Classification Search
CPC .................................. A61B 5/36; A61B 5/271
(Continued)

(56) References Cited

U.S. PATENT DOCUMENTS

2003/0073914 A1*  4/2003  Taha ...................... A61B 5/366
                                                                     600/509
2016/0100803 A1*  4/2016  Korzinov ............... A61B 5/389
                                                                     600/301
(Continued)

FOREIGN PATENT DOCUMENTS

CN      110200621 A    9/2019
JP    2019-097639 A    6/2019
(Continued)

OTHER PUBLICATIONS

Qingxue Zhang et al., "All-ECG: A Least-number of Leads ECG Monitor for Standard 12-lead ECG Tracking during Motion" 2019 IEEE Healthcare Innovations, Nov. 20, 2019.
(Continued)

*Primary Examiner* — Nicole F Lavert
*Assistant Examiner* — Nicole F Johnson
(74) *Attorney, Agent, or Firm* — WOMBLE BOND DICKINSON (US) LLP

(57) ABSTRACT

Embodiments of the present disclosure provide a mobile electrocardiogram (ECG) sensor comprising an electrode assembly comprising electrodes, wherein the electrode assembly senses heart-related signals when in contact with a body of a user, and produces electrical signals representing the sensed heart-related signals. The ECG sensor further comprises a processing device, operatively coupled to the electrode assembly, the processing device to provide the sensed heart-related signals to a machine learning module trained to predict a twelve-lead QT interval (QTc) value from the mobile ECG sensor comprising less than twelve leads. The ECG sensor also comprises a housing containing the electrode assembly and the processing device.

25 Claims, 11 Drawing Sheets

(58) Field of Classification Search
USPC .......................................................... 600/509
See application file for complete search history.

(56) References Cited

U.S. PATENT DOCUMENTS

| | | |
|---|---|---|
| 2016/0135708 A1* | 5/2016 | Chakravarthy ...... A61B 5/7275 600/515 |
| 2017/0105683 A1 | 4/2017 | Xue |
| 2021/0100471 A1 | 4/2021 | Yu et al. |
| 2021/0169392 A1 | 6/2021 | Albert et al. |
| 2022/0287613 A1 | 9/2022 | Albert |

FOREIGN PATENT DOCUMENTS

| | | | |
|---|---|---|---|
| WO | 1999055228 | 11/1999 | |
| WO | WO-2015107184 A1 * | 7/2015 | ............. A61B 5/333 |
| WO | 2019217556 A1 | 11/2019 | |

OTHER PUBLICATIONS

Hussein Atoui et al., "A Novel Neural-Network Model for deriving Standard 12-Lead ECGs From Serial Three-Lead ECGs: Application to Self-Care" IEEE Transactions on Information Technology in Biomedicine, Apr. 8, 2010.

The International Preliminary Report on Patentability for International Application No. PCT/US2021/039118 mailed on Dec. 13, 2022.

First Office Action from related Japanese Patent Application No. JP2022-580467 mailed on Apr. 22, 2025, 4 pages.

* cited by examiner

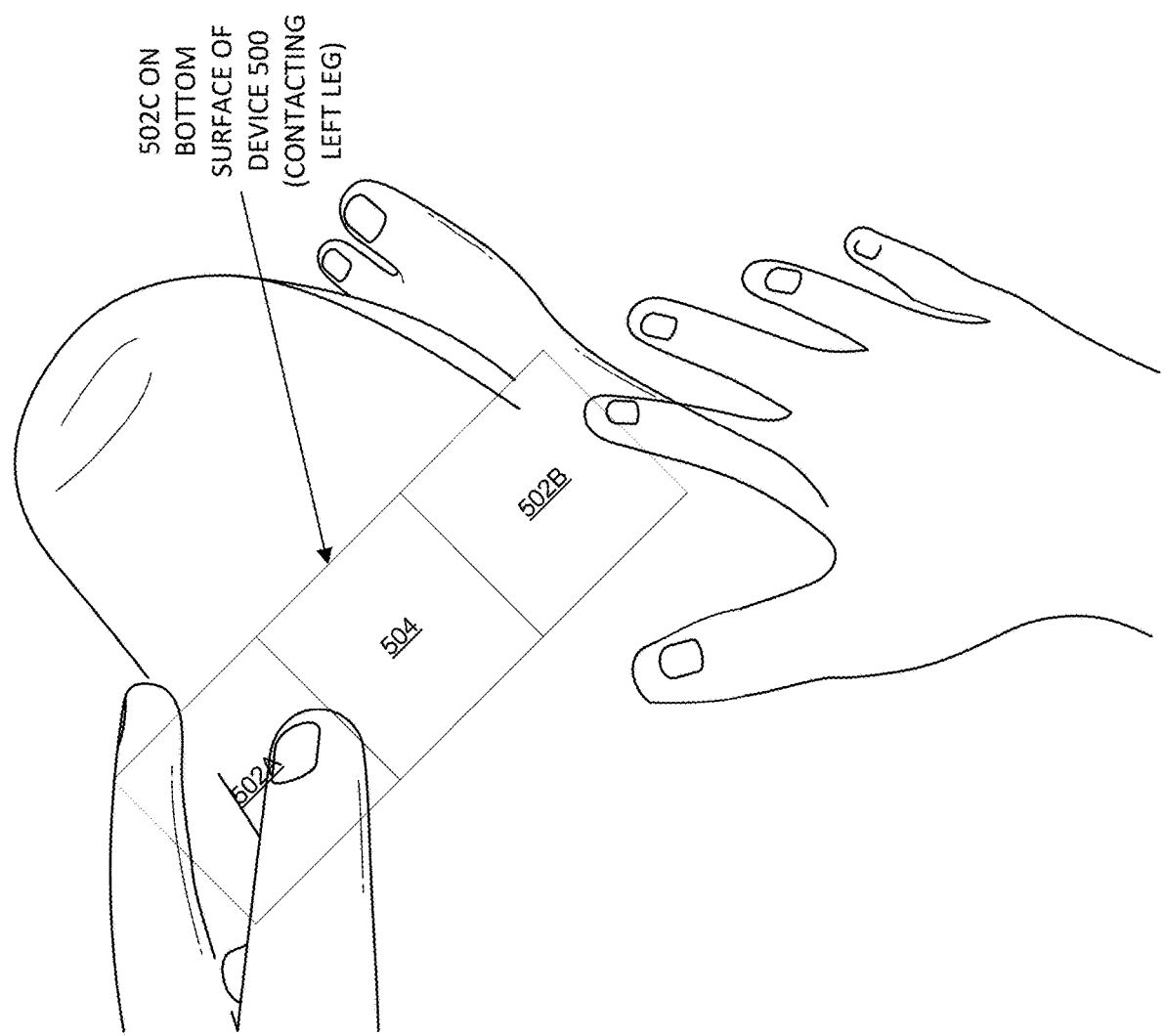

TWO-LEAD QT INTERVAL PREDICTION

CROSS-REFERENCE TO RELATED APPLICATIONS

This application claims the benefit of U.S. Provisional Application No. 63/044,882, filed Jun. 26, 2020 and entitled TWO-LEAD QT INTERVAL PREDICTION, the contents of which are hereby incorporated by reference in their entirety.

BACKGROUND

It is estimated that by 2030, over 23 million people will die from cardiovascular diseases annually. Cardiovascular diseases are prevalent in across populations of first world as well as third world countries and regardless of socioeconomic status. Monitoring of cardiovascular function can aid in the treatment and prevention of cardiovascular disease. For example, a patient with A-fib (or other type of arrhythmia) can be monitored for extended periods of time to manage the disease using a Holter monitor or other ambulatory electrocardiography device. Such devices can continuously monitor the electrical activity of the cardiovascular system for e.g., at least 24 hours. Such monitoring can be critical in detecting conditions such as acute coronary syndrome (ACS), among others.

The mammalian heart generates and conducts an electric current that signals and initiates the coordinated contraction of the heart. In humans, an electrical signal is produced by a portion of the heart known as the SA node. After being generated by the SA node, the electric current travels throughout the myocardium in a manner that is predictable in a healthy heart.

In general, an electrocardiogram (ECG) is a graphic representation of the electric conduction of the heart over time as projected on the surface of the body. An ECG is typically displayed on a graph having an x and y axis. Typically, the x-axis of an ECG displays time and the Y-axis of an ECG displays the electric potential (in millivolts) of an electric current that is conducted through the heart during normal cardiac function.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5C illustrates the use of the ECG sensing device of FIG. 5A to measure the limb leads of a user, in accordance with some embodiments of the present disclosure.

DETAILED DESCRIPTION

It is to be understood that the present disclosure is not limited in its application to the details of construction, experiments, exemplary data, and/or the arrangement of the components set forth in the following description. The embodiments of the present disclosure are capable of other embodiments or of being practiced or carried out in various ways. Also, it is to be understood that the terminology employed herein is for purpose of description and should not be regarded as limiting.

An electrocardiogram (ECG) provides a number of ECG waveforms that represent the electrical activity of a person's heart. An ECG monitoring device may comprise a set of electrodes for recording these ECG waveforms (also referred to herein as "taking an ECG") of the patient's heart. The set of electrodes may be placed on the skin of the patient in multiple locations and the electrical signal (ECG waveform) recorded between each electrode pair in the set of electrodes may be referred to as a lead. Varying numbers of leads can be used to take an ECG, and different numbers and combinations of electrodes can be used to form the various leads. Example numbers of leads used for taking ECGs are 3, 5, and 12 leads.

Figure 1:
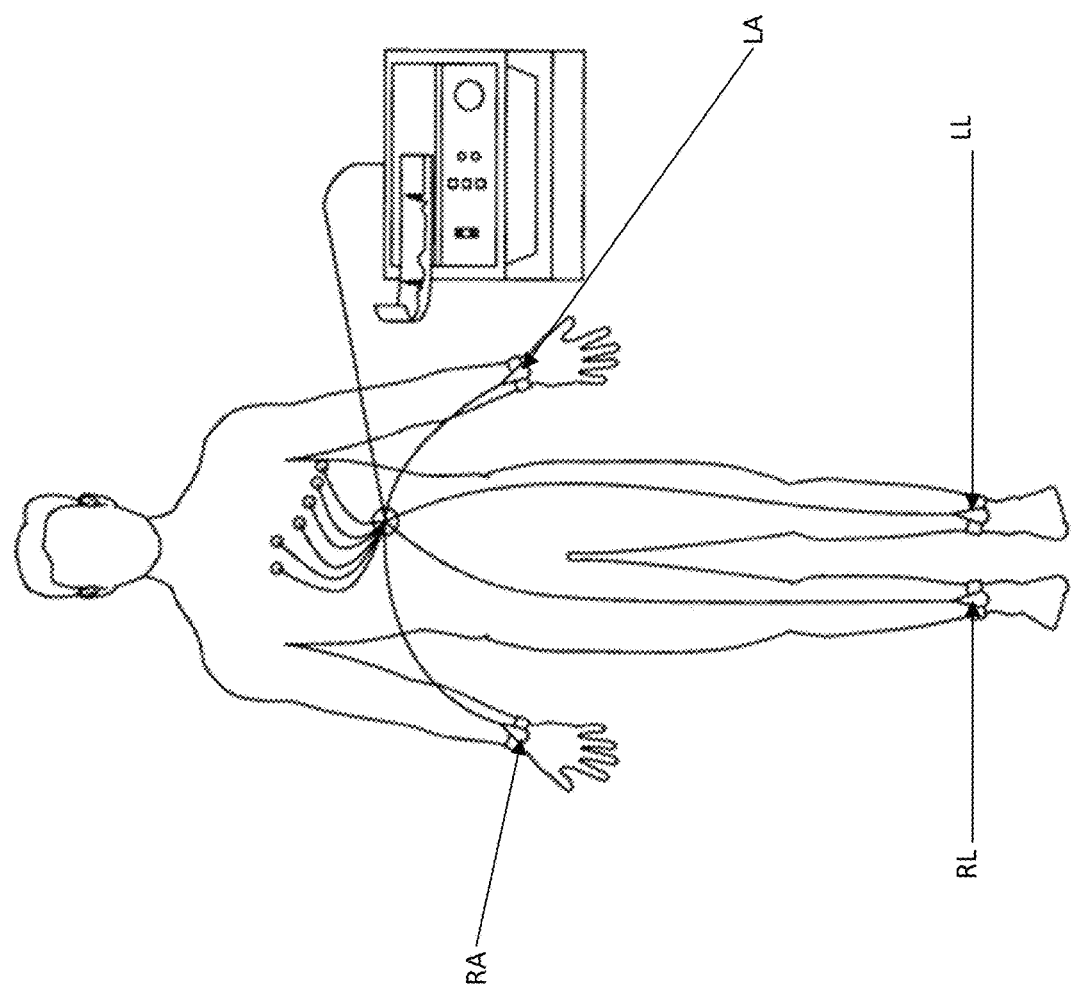
FIG. 1 is a pictorial representation of a prior art electrocardiograph having 10 electrodes positioned on a patient's body for taking a prior art 12-lead electrocardiogram, in accordance with some embodiments of the present disclosure.

FIG. 1 is a pictorial representation of the 10 electrodes of a conventional ECG sensing device being placed on the patient for obtaining a standard 12-lead ECG. The electrode placed on the right arm is commonly referred to as RA. The electrode placed on the left arm is referred to as LA. The RA and LA electrodes are placed at the same location on the left and right arms, preferably but not necessarily near the wrist. The leg electrodes can be referred to as RL for the right leg and LL for the left leg. The RL and LL electrodes are placed on the same location for the left and right legs, preferably but not necessarily near the ankle.

Figure 2:
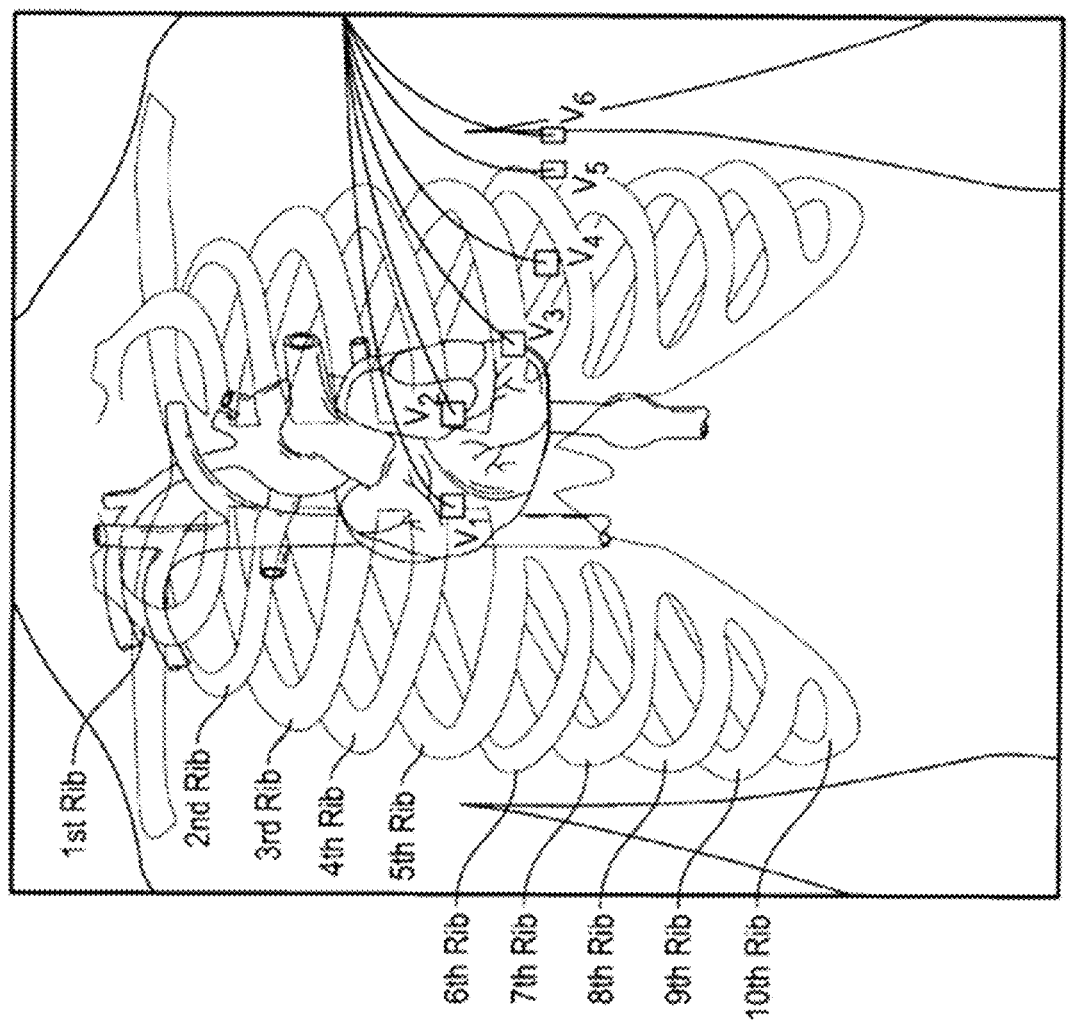
FIG. 2 is a pictorial representation of a chest showing an example of electrode placement on the chest for taking a prior art 12-lead electrocardiogram, in accordance with some embodiments of the present disclosure.

FIG. 2 illustrates the placement of the six electrodes on the chest with the six electrodes being labeled $V_1$, $V_2$, $V_3$, $V_4$, $V_5$, and $V_6$ respectively. $V_1$ is placed in the fourth intercostal space, for example between ribs 4 and 5, just to the right of the sternum. $V_2$ is placed in the fourth intercostal space, for example between ribs 4 and 5, just to the left of the sternum. $V_3$ is placed in the fifth intercostal space midway between electrodes $V_2$ and $V_4$. $V_4$ is placed in the fifth intercostal space between ribs 5 and 6 on the left mid-clavicular line. $V_5$ is placed horizontally even with $V_4$ on the left anterior axillary line. $V_6$ is placed horizontally even with $V_4$ and $V_5$ on the left mid-axillary line.

The electrocardiograph then calculates and outputs three limb lead waveforms. Limb leads I, II, and III are bipolar leads having one positive and one negative pole. Lead I is the voltage between the left arm (LA) and right arm (RA), e.g. I=LA−RA. Lead II is the voltage between the left leg (LL) and right arm (RA), e.g. II=LL−RA. Lead III is the voltage between the left leg (LL) and left arm (LA), e.g. III=LL−LA. Leads I, II and III are commonly referred to as "limb leads."

Unipolar leads also have two poles; however, the negative pole is a composite pole made up of signals from multiple other electrodes. In a conventional cardiograph for obtaining a 12-lead ECG, all leads except the limb leads are unipolar (aVR, aVL, aVF, $V_1$, $V_2$, $V_3$, $V_4$, $V_5$, and $V_6$). Augmented limb leads (aVR, aVL, and aVF) view the heart from different angles (or vectors) and are determined from electric potential differences between one of RA, LA, and LL, and a composite comprising of two of RA, LA, and LL. Thus, three electrodes positioned at RA, LA, and LL will sense aVR, aVL, and aVF simultaneously based on the above relationships. Which is to say that while leads, I, II, and III each require input from only two electrodes, and aVR, aVL, and aVF may require input from three electrodes positioned at RA, LA, and LL.

For example, the augmented vector right (aVR) positions the positive electrode on the right arm, while the negative electrode is a combination of the left arm electrode and the left leg electrode, which "augments" the signal strength of the positive electrode on the right arm. Thus the augmented vector right (aVR) is equal to RA−(LA+LL)/2 or −(I+II)/2. The augmented vector left (aVL) is equal to LA−(RA+LL)/2 or (I−II)/2. The augmented vector foot (aVF) is equal to LL−(RA+LA)/2 or (II−I)/2.

In one embodiment, the six electrodes on the chest of the patient are close enough to the heart that they do not require augmentation. A composite pole called Wilson's central terminal (often symbolized as CTw, Vw, or WCT) is used as the negative terminal. Wilson's central terminal is produced by connecting the electrodes RA, LA, and LL together, via a simple resistive network, to give an average potential across the body, which approximates the potential at an infinite distance (i.e. zero). Wilson's central terminal, WCT, is calculated as (RA+LA+LL)/3.

The ECG waveforms (each one corresponding to a lead of the ECG) recorded by the ECG monitoring device may comprise data corresponding to the electrical activity of the person's heart. A typical heartbeat may include several variations of electrical potential, which may be classified into waves and complexes, including a P wave, a QRS complex, a T wave, and a U wave among others, as is known in the art. Stated differently, each ECG waveform may include a P wave, a QRS complex, a T wave, and a U wave among others, as is known in the art. The shape and duration of these waves may be related to various characteristics of the person's heart such as the size of the person's atrium (e.g., indicating atrial enlargement) and can be a first source of heartbeat characteristics unique to a person. Each wave or a complex of multiple waves (i.e. the QRS complex) is associated with a different phase of the heart's depolarization and repolarization. The ECG waveforms may be analyzed (typically after standard filtering and "cleaning" of the signals) for various indicators that are useful in detecting cardiac events or status, such as cardiac arrhythmia detection and characterization. Such indicators may include ECG waveform amplitude and morphology (e.g., QRS complex amplitude and morphology), R wave-ST segment and T wave amplitude analysis, and heart rate variability (HRV), for example.

Figure 3:
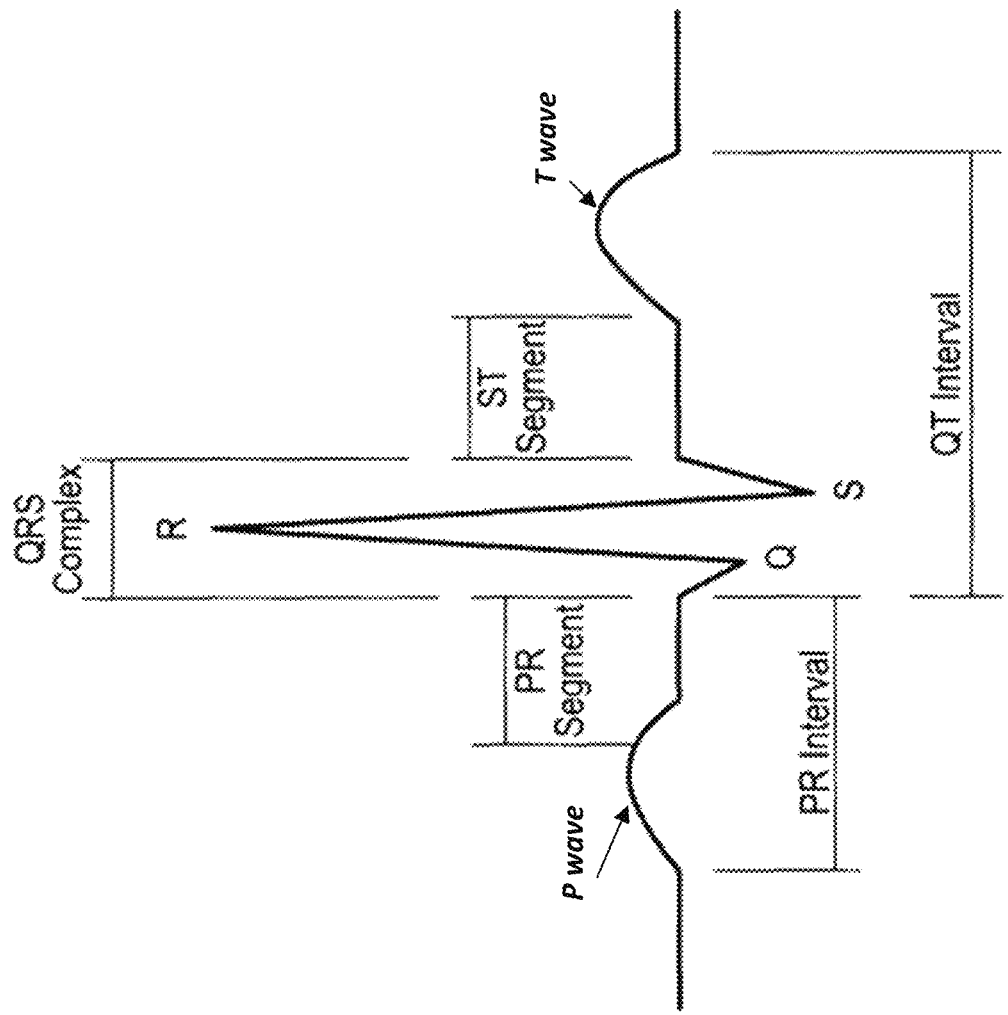
FIG. 3 illustrates an example Lead I annotated to show PQRST waves generated by a 12-lead electrocardiograph, in accordance with some embodiments of the present disclosure.

FIG. 3 illustrates an example Lead I annotated to show P, QRS, and T waves/complexes generated by a 12-lead electrocardiograph. Typically, an ECG of a normal beating heart has a predictable wave-form in each of the twelve ECG leads. ECG portions between two waves are referred to as segments and ECG portions between more than two waves are referred to as intervals.

For example, the ECG portion between the end of the S wave (part of QRS complex) and the beginning of the T wave is referred to as the ST segment while the portion of the ECG between the beginning of the Q wave (part of QRS complex) and the end of the T wave is referred to as the QT interval.

Figure 4:
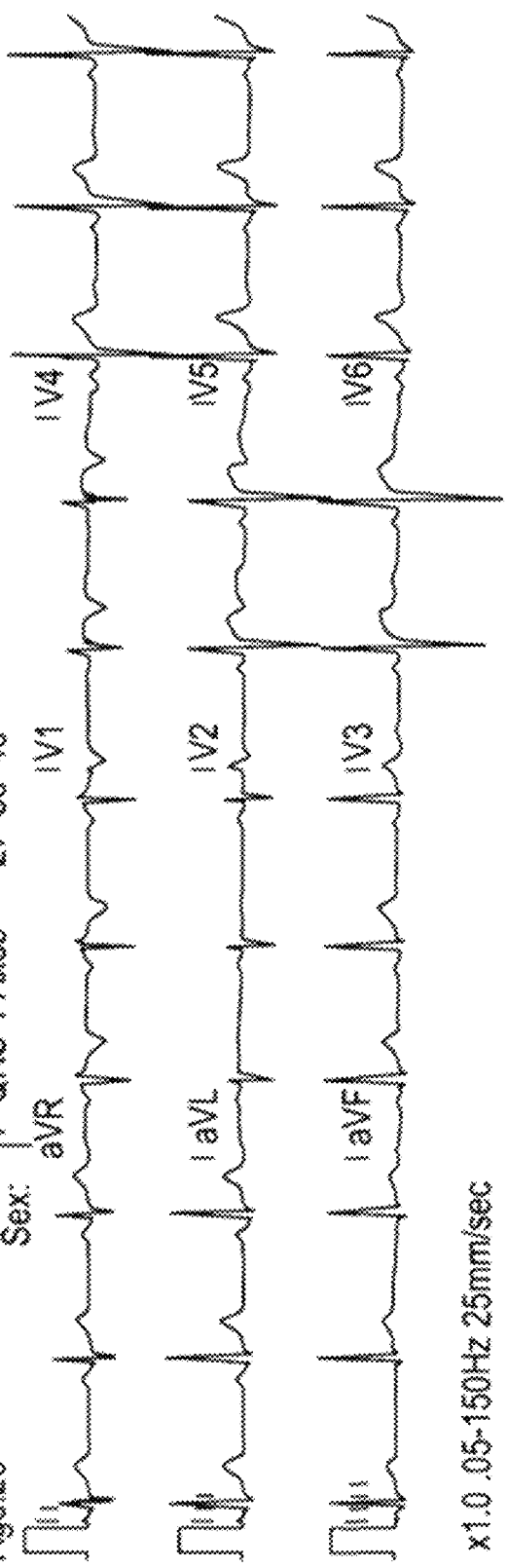
FIG. 4 shows an example 12-lead electrocardiogram in a conventional format, in accordance with some embodiments of the present disclosure.

FIG. 4 shows an example 12-lead electrocardiogram in a conventional format. As shown in FIG. 4, for standard ECG waveform tracing, twelve ECG leads are displayed individually on an X and Y axis, wherein the Y-axis represents time and the X-axis represents voltage. In these tracings, all twelve ECG waveforms are aligned with respect to their X-axes. That is, the P, QRS, and T waveforms of all the leads all occur at the same time along the X-axis of each of the respective tracings. For example, in a traditional ECG waveform tracing, if a QRS complex occurs at 1 second on the X-axis in the lead I waveform tracing, a QRS complex occurs at 1 second in each of the other eleven ECG waveforms (i.e. leads II, III, aVR, aVL, aVF, V1, V2, V3, V4, V5, and V6).

The standard time aligned format allows health care providers to more easily obtain information from the twelve sensed ECG waveforms. In the traditional ECG tracing, time alignment is facilitated by virtue of the waveforms being sensed simultaneously by the ten electrodes of the traditional ECG that are all simultaneously positioned on the skin of the individual whose ECG is sensed. That is, because all twelve ECG leads of a traditional ECG are sensed simultaneously, time-alignment is achieved by simply displaying all of the waveforms together on identical axes.

It should be noted that a set of two or more leads may be analyzed to derive information to generate a full, 12-lead ECG. Such transformation may be performed using a machine learning model (e.g., a neural network, deep-learning techniques, etc.). The machine learning model may be trained using 12-lead ECG data corresponding to a population of individuals. The data, before being input into the machine learning model, may be pre-processed to filter the data in a manner suitable for the application. For example, data may be categorized according to height, gender, weight, nationality, etc. before being used to train one or more machine learning models, such that the resulting one or models are finely-tuned the specific types of individuals. In a further embodiment, the machine learning model may be further trained based on a user's own ECG data, to fine-tune and personalize the model even further to decrease any residual synthesis error.

While a conventional 12-lead electrocardiogram gives very useful information concerning the health and condition of an individual's heart, the conventional electrocardiograph equipment is expensive and the procedure is not normally available in areas other than hospitals and medical doctors' offices. Therefore, monitoring is not done frequently even in first world countries, and in poorer areas of the world an electrocardiograph may not even be available.

Figure 5A:
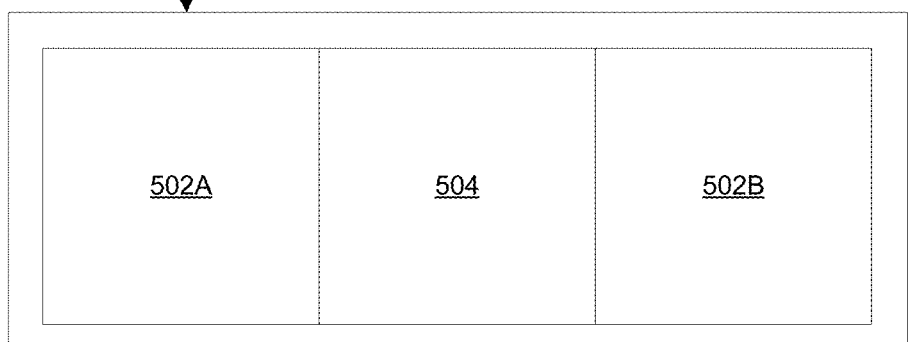
FIG. 5A shows an exemplary ECG sensing device, in accordance with some embodiments of the present disclosure.

FIG. 5A shows top and bottom views of an exemplary ECG sensing device 500 comprising a set of electrodes 502 (also referred to as an electrode assembly) in accordance with some embodiments of the present disclosure. In some embodiments, one or more capacitive electrodes are used in the ECG sensing device 500 so that, for example, the capacitive electrode senses an electric potential through a garment worn over the body of the user. Similarly, a conductive spray or gel may be placed on the body of the user so that a typical electrode senses an electric potential through a garment worn over the body of the user.

In one embodiment, the ECG sensing device 500 is constructed, in whole or in part, from stainless steel or some other suitable material. In one embodiment, the ECG device 500 includes an exterior coating, such as Titanium Nitride or other suitable coating. Advantageously, such materials may increase biocompatibility and optimize electrode characteristics.

In one embodiment, device 500 is referred to as a mobile computing device herein, and includes all necessary components to sense, record, and display ECG signals and analysis. In another embodiment, device 500 connects via wires or wirelessly to a separate mobile computing device (e.g., computing device 550). In such a case, the device 500 may sense the ECG signals and send the unmodified or modified signals to a mobile computing device for further analysis and/or display. In yet another embodiment, any combination of the two examples listed above is possible. For example, although the ECG sensing device 500 may be considered a self-contained mobile computing device, capable of performing all operations described herein, ECG sensing device 500 may still connect to, and interact with, a second mobile computing device for any suitable purpose (offloading processing/analysis, display, etc.).

The ECG sensing device 500 may include one or more controls and/or indicators. For example, the device 500 may include buttons, dials, etc. to select functions (e.g., turning on/off ECG reading, to begin to transmit ECG information, etc.). The ECG sensing device 500 may further include a display that displays a recorded ECG.

The ECG sensing device 500 may include a housing 520, where two electrodes 502A and 502B are positioned on a top surface of the housing 520 and a third electrode 502C is positioned on a bottom surface of the housing 520 as shown in FIG. 5A. The electrodes 502 may be insulated from each other via dialectrics 504 or other suitable materials such that they are able to sense and record distinct signals. In some embodiments, the electrodes 502 may be comprised of silver-silver chloride (or some other suitable material) electrodes. In some embodiments, ECG sensing device 500 may include an electrode connector (not shown) such as e.g., a female socket on one end or a side allowing one or more ECG electrodes to be connected to the ECG sensing device 500 to be used on skin with an adhesive or without an adhesive (e.g., a conductive gel and the electrodes 502).

Figure 5B:
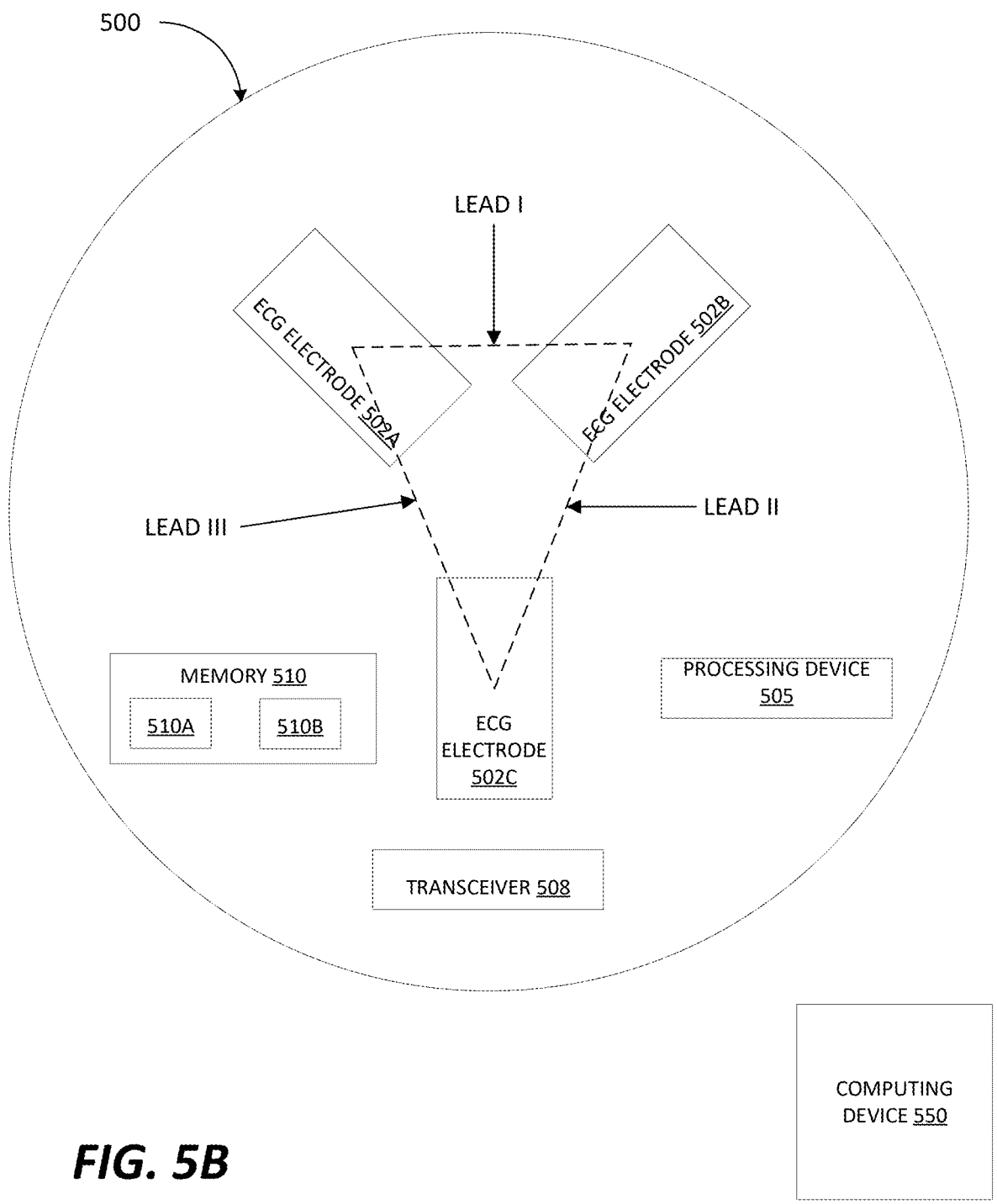
FIG. 5B is a hardware block diagram of the ECG sensing device of FIG. 5A, in accordance with some embodiments of the present disclosure.

FIG. 5B illustrates a hardware block diagram of ECG sensing device 500, which may include hardware such as processing device 505 (e.g., processors, central processing units (CPUs)), memory 510 (e.g., random access memory (RAM), storage devices (e.g., hard-disk drive (HDD)), solid-state drives (SSD), etc.), and other hardware devices (e.g., analog to digital converter (ADC) etc.). A storage device may comprise a persistent storage that is capable of storing data. A persistent storage may be a local storage unit or a remote storage unit. Persistent storage may be a magnetic storage unit, optical storage unit, solid state storage unit, electronic storage units (main memory), or similar storage unit. Persistent storage may also be a monolithic/single device or a distributed set of devices. In some embodiments, the processing device 505 may comprise a dedicated ECG waveform processing and analysis chip that provides built-in leads off detection. The ECG sensing device 500 may include an ADC (not shown) having a high enough sampling frequency for accurately converting the ECG waveforms measured by the set of electrodes 502 into digital signals (e.g., a 24 bit ADC operating at 500 Hz or higher) for processing by the processing device 505.

The memory 510 may include a lead synthesis software module 510A (hereinafter referred to as module 510A) and an QT prediction software module 510B (hereinafter referred to as module 510B). The processing device 205 may execute the module 207A to synthesize ECG waveforms corresponding to leads that were not measured by the electrodes of the ECG sensing device 500 as discussed in further detail herein. The processing device 505 may execute the module 510B to accurately predict a QT interval of a user, as discussed in further detail herein.

The ECG sensing device 500 may further comprise a transceiver 508, which may implement any appropriate protocol for transmitting ECG data wirelessly to one or more local and/or remote computing devices (e.g., computing device 550). For example, the transceiver 508 may comprise a Bluetooth™ chip for transmitting ECG data via Bluetooth to local computing devices (e.g., a laptop or smart phone of the user). In other embodiments, the transceiver 508 may include (or be coupled to) a network interface device configured to connect with a cellular data network (e.g., using GSM, GSM plus EDGE, CDMA, quadband, or other cellular protocols) or a WiFi (e.g., an 802.11 protocol) network, in order to transmit the ECG data to a remote computing device (e.g., a computing device of a physician or healthcare provider) and/or a local computing device.

As discussed in further detail herein, the computing device 550 may be used to provide instructions for operating the ECG sensing device 500, or may correspond to a healthcare provider system to which ECG data measured by the ECG sensing device 500 is to be transmitted, for example.

As shown in FIG. 5C, in one practical example, a user holds the device with one or both hands so that each hand contacts an electrode 502A and 502B on the ECG sensing device 500 while the left leg contacts electrode 502C. The ECG sensing device 500 (with, optionally, a separate mobile computing device) may then be used to record Lead I, Lead II, and Lead III, from which at least three additional leads may be determined (e.g., by executing module 510A), as described in further detail herein. Specifically, the augmented leads, aVR, aVL, and aVF, may be determined using Leads I, II, and III. The user may be sitting, standing, or in any position of comfort.

Figure 5D:
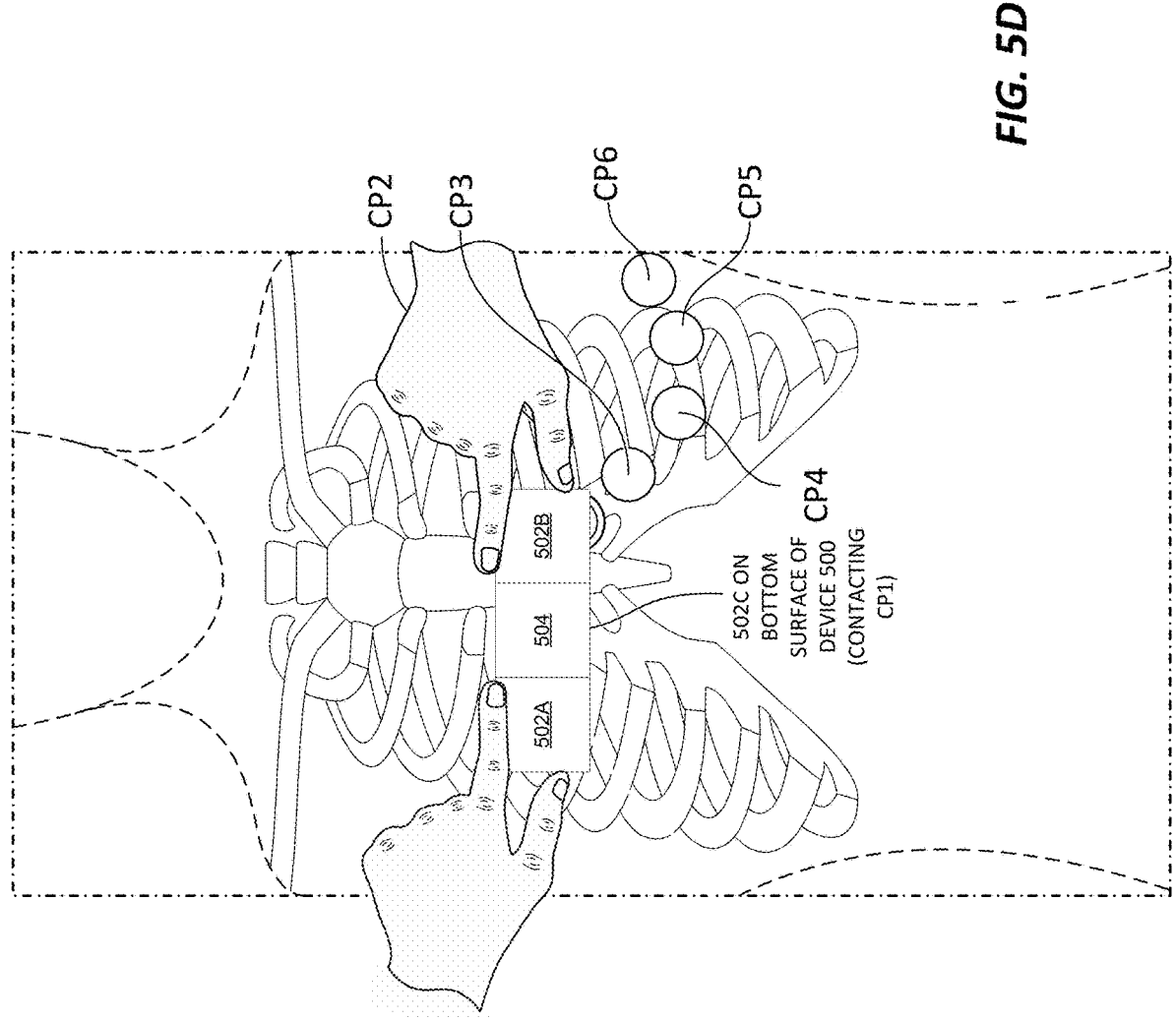
FIGS. 5D and 5E illustrate the use of the ECG sensing device of FIG. 5A to measure the precordial leads of the user, in accordance with some embodiments of the present disclosure.
Figure 5E:
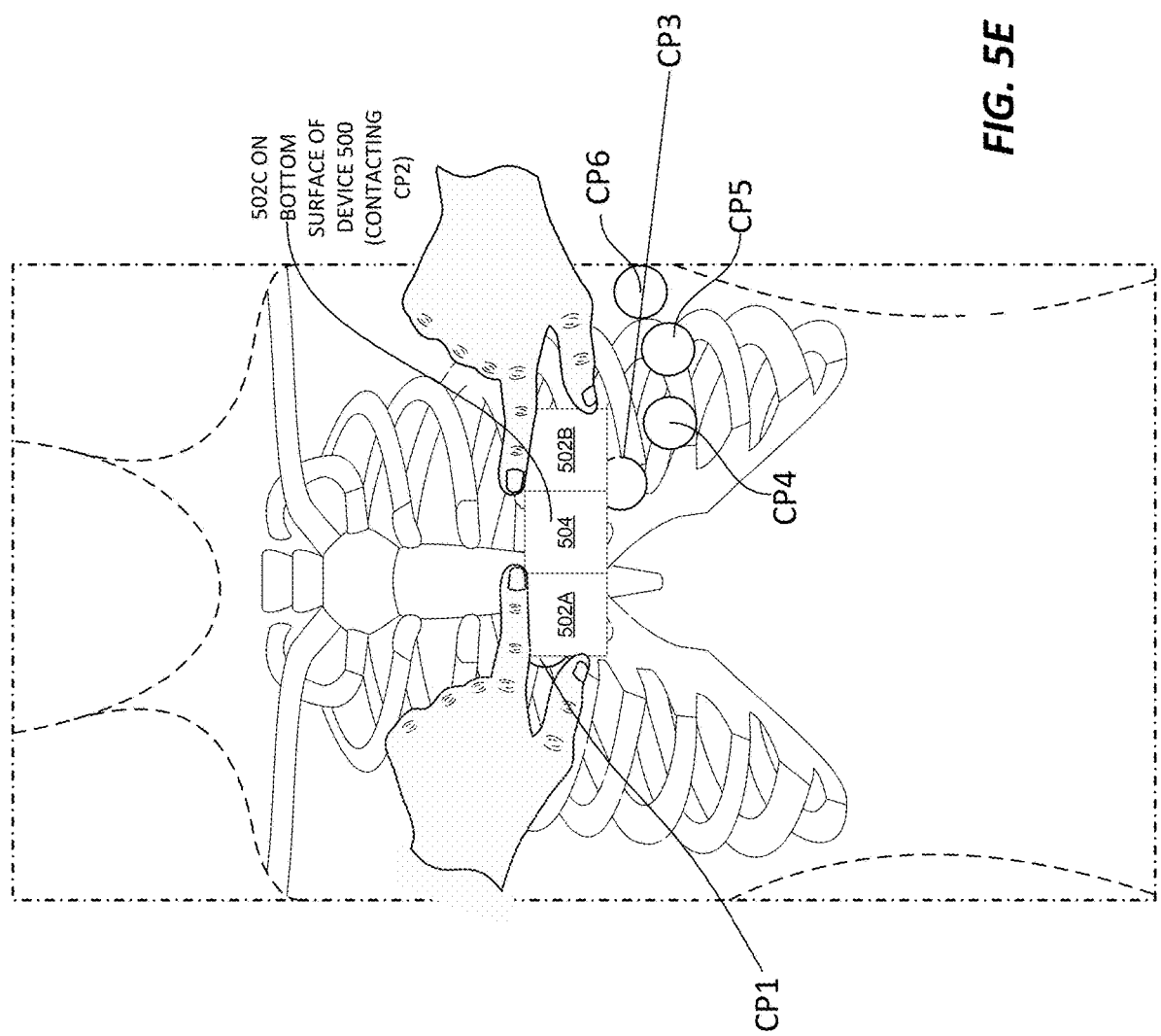

FIGS. 5D and 5E illustrate an embodiment where a user may also record the precordial leads V1, V2, V3, V4, V5, and V6 using the ECG sensing device 500 as described herein. A user may hold the ECG sensing device 500 so that each hand of the user contacts an electrode 502A and 502B while the third electrode (e.g., 502C) is held against the chest so as to contact one of the six precordial chest positions which are represented as "CP1," "CP2," "CP3," "CP4," "CP5," and "CP6". For example, the user may start with the ECG sensing device 500 positioned such that electrode 502C is contacting CP1 and from here, the user may move the ECG sensing device 500 such that it sequentially makes contact with each of the six electrode positions corresponding to leads V2, V3, V4, V5, and V6. In some embodiments, while the user contacts an electrode 502A and 502B of the ECG sensing device 500 with each of his right and left hands and simultaneously holds the third electrode (e.g., 502C) of the device 500 against a positon on his chest corresponding to V1, V2, V3, V4, V5, and V6, each of the electric potentials sensed at the chest positions corresponding to V1, V2, V3, V4, V5, and V6 are sensed simultaneously with an electric potential sensed at LA and RA. Lead I is equivalent to the potential difference between LA and RA. Thus, in some embodiments, measuring an electric potential at a position on the chest corresponding to any of V1, V2, V3, V4, V5, and V6 together with the electric potential at the LA and RA positions is equivalent to the difference in potential at the chest position and lead I. That is, for example, using all three electrodes of device 500 as described, V1 (the electric potential at the V1 chest position)=("CP1")−WCT (WCT=(RA+LA+LL)/3 or (lead I+lead II)/3).

The six precordial chest positions can be represented as ("CP1," "CP2," "CP3," "CP4," "CP5," and "CP6") and a composite value known as Wilson's Central Terminal ("WCT"). "CP(x)" corresponds to any of the six potentials sensed at the anatomical precordial lead positions (where "x" is a position number 1-6). For example, CP1 is the ECG measurement sensed at a location at which an electrode is placed to measure V1, and that position is approximately in the second intercostal space immediately to the right of the sternum. Thus, lead V1=CP1−WCT.

WCT is equal to one third of the sum of the potentials sensed at the right upper extremity, left upper extremity, and left lower leg or ⅓(RA+LA+LL). In a standard ECG that uses ten simultaneously placed electrodes, a WCT value is generated at the same time that a precordial lead is sensed, because RA, LA, LL, which determine WCT, are sensed at the same time as CPI, CP2, CP3, CP4, CP5, and CP6.

In these embodiments, the electrodes 502 are positioned and configured to simultaneously sense/calculate the six limb leads leads I, II, III, aVR, aVL, and aVF when a user contacts a first electrode 502A with a right upper extremity, a second electrode 502B with a left upper extremity, and a third electrode 502C with a left lower extremity.

As also described herein, an ECG sensing device 500 is configured to sense the six leads V1, V2, V3, V4, V5, and V6 sequentially when a user, for example, contacts a first electrode 502A with a right upper extremity, a second electrode 502B with a left upper extremity, and a third electrode 502C with an area of his or her chest corresponding to a precordial lead position.

In some embodiments in which the ECG sensing device 500 comprises three electrodes as described herein, the RA, LA, LL, which determine WCT, are not sensed simultaneously with one or more precordial leads. That is, when one of the three electrodes of the ECG sensing device 500 is held against the chest wall of a user, only two electrodes remain free and a traditional WCT cannot be simultaneously determined. In some of these embodiments, RA is set to 0. When RA=0, it provides a WCT=(0+LA+LL)/3 or ((LA−0)+(LL−0))/3 which can be further expressed as WCT=(lead I+lead II)/3.

Likewise, in these embodiments, wherein RA is set to 0, an averaged WCT=(averaged lead I+averaged lead II)/3. An averaged WCT in some embodiments is generated using an averaged lead I and an averaged lead II that are generated using, for example, an ensemble averaging method on the lead I and lead II waveforms sensed by the ECG sensing device described herein. Generating an average WCT is beneficial in, for example, signal filtering and also simplifies alignment of values for purposes of subtraction. That is, in some embodiments, CPI, CP2, CP3, CP4, CP5, and CP6 are each averaged and an averaged WCT is respectively subtracted from each to generate V1, V2, V3, V4, V5, and V6.

A number of machine learning (ML) methods may also be used to synthesize the full 12 lead set from the set of leads measured by the ECG sensing device 500. ML is well suited for continuous monitoring of one or multiple criteria to identify anomalies or trends, big and small, in input data as compared to training examples used to train the model. The ML model described herein may be trained on user data from a population of users, and/or trained on other training examples to suit the design needs for the model. ML models that may be used with embodiments described herein include by way of example and not limitation: Bayes, Markov, Gaussian processes, clustering algorithms, generative models, kernel and neural network algorithms. Some embodiments utilize a machine learning model based on a trained neural network (e.g., a trained recurrent neural network (RNN) or a trained convolution neural network (CNN)).

For example, the ML model may utilize artificial neural networks (ANNs) for supervised classification, where the outcome of the model represents the probability of the input sample to be in a specific class of data or exhibits some peculiar characteristics. In another example, a data driven approach based on convolutional neural networks (CNNs) is used. By using convolution operations, the ML model may take into account the correlation among temporally closed input samples to infer a single output data point. More specifically, a single output sample (each precordial lead) at a generic time t is affected by all the input samples (all limb leads) from t−τ to t+τ. The value of τ, which represents the receptive field of the network, highly depends on the model architecture and typically increases with its depth, i.e., the number of consecutive layers. The ability to generalize on unseen data, and avoid overfitting issues, is of primary importance for all data driven approaches. Complex models, along with small datasets, may lead to excellent performance on the training set, but may perform poorly on unseen data. Any appropriate regularization method may be used to optimize the model, such as inter and intra-layer normalization (e.g., batch normalization and layer normalization), and data augmentation techniques. Finally, to improve the effectiveness and efficiency of the model, the use of residual connections, i.e., an identity mapping that allow gradients to flow through a layer during the backpropagation of gradient-based optimization algorithms may be utilized.

The use of AI/deep learning with multi-lead ECG sensing devices may allow patients themselves (in hospital or at home) to monitor the electrical activity of their heart without the need for hospital visits or bulky hardware.

In some embodiments, the memory 510 of the ECG sensing device 500 or another mobile computing device (e.g., computing device 550) may include an instruction software module (not shown) that displays or otherwise transmits instructions to an individual instructing the user as to how to position the ECG sensing device 500 in order to perform an ECG (e.g., over the standard precordial lead chest positions) as well as a position in which the user should be situated in order to perform an ECG. For example, a display may show an image of a location on the user's chest against which the user is instructed to hold the third electrode while holding electrodes one and two with his left and right hands respectively.

In some embodiments, software on the ECG sensing device 500 or computing device 550 is configured to recognize if a first electrode is contacted by a left hand and second electrode is being contacted by a right hand versus whether a first electrode is contacted by a right hand a second electrode is contacted by a left hand. For example, in some embodiments, a third electrode is positioned on a different surface of the ECG sensing device 500 than the first and second electrodes, such that a user will likely need to swap hand positions to contact the precordial lead positions on their chest with the third electrode after contacting their left leg with the third electrode. In some embodiments, software on the ECG sensing device 500 or other mobile computing device receives information from a sensor coupled with or integrated with an ECG sensing device 500, wherein the sensor provides information about the position of the device in space. Examples of the class of sensors that sense such information include but are not limited to accelerometers, inclinometers, and gyrometers.

In some embodiments, the ECG sensing device 500 is configured to sense an ECG when one or more of the electrodes 502 are not engaged by the user. For example, in some embodiments, the ECG sensing device 500 comprises three electrodes, and the ECG sensing device 500 is configured to sense an ECG when either all three electrodes are engaged by the user or when any two of the three electrodes are engaged by the user. That is, in this embodiment, when a user, for example, contacts a skin surface on their right upper extremity with a first electrode and contacts a skin surface on their left upper extremity with a second electrode, but does not contact the third electrode, the ECG sensing device senses an ECG. When, in this example, the two of three electrodes are contacted by a right and left upper extremity respectively, a lead I is sensed. Likewise, when the two of three electrodes are contacted by a right upper extremity and left lower extremity respectively, a lead II is sensed. Likewise, when the two of three electrodes are contacted by a left upper extremity and left lower extremity respectively, a lead III is sensed. In this embodiment, the ECG sensing device 500 recognizes that one or more of the electrodes have not been contacted by a user while two or more electrodes have been contacted by the user, by, for example, sensing an electrode potential from two or more electrodes that are contacted but not sensing an electrode potential from electrodes that are not contacted by the user.

In some embodiments of the ECG sensing devices described herein, exemplary embodiments of which are shown in FIGS. 5A-5E, a mobile computing device (e.g., computing device 550) is configured to run a software application as described herein. In further embodiments, the mobile computing device includes one or more hardware central processing units (CPUs) or general purpose graphics processing units (GPGPUs) that carry out the device's functions. In still further embodiments, the mobile computing device further comprises an operating system configured to perform executable instructions. In some embodiments, the mobile computing device is optionally connected a computer network. In further embodiments, the mobile computing device is optionally connected to the Internet such that it accesses the World Wide Web. In still further embodiments, the mobile computing device is optionally connected to a cloud computing infrastructure. In other embodiments, the mobile computing device is optionally connected to an intranet. In other embodiments, the mobile computing device is optionally connected to a data storage device.

In accordance with the description herein, suitable mobile computing devices include, by way of non-limiting examples, server computers, desktop computers, laptop computers, notebook computers, sub-notebook computers, netbook computers, netpad computers, handheld computers, smartphone, smartwatches, digital wearable devices, and tablet computers.

In some embodiments, the mobile computing device includes an operating system configured to perform executable instructions. The operating system is, for example, software, including programs and data, which manages the device's hardware and provides services for execution of applications. Non-limiting examples of suitable operating systems include FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing.

In some embodiments, a mobile computing device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the mobile computing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes, optical disk drives, and cloud computing based storage. In further embodiments, the storage and/or memory device is a combination of devices such as those disclosed herein.

In some embodiments, the mobile computing device includes a display to send visual information to a user. In some embodiments, the mobile computing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In still further embodiments, the input device is a combination of devices such as those disclosed herein.

In various embodiments, the platforms, systems, media, and methods described herein include a cloud computing environment. In some embodiments, a cloud computing environment comprises a plurality of computing processors.

It should be understood that while FIGS. 5A-5E show exemplary embodiments of the user matter described herein, generally, numerous electrode positions, shapes, and sizes may be used in the devices described herein so that an individual comfortably and naturally contacts the electrodes. For example, all three electrodes may be positioned entirely on the sides of a computing device or a device cover.

In any of the embodiments shown in FIGS. 5A-5E, one or more electrodes may be configured to be removable from the ECG sensing device 500. In these embodiments the ECG sensing device has, for example, either a male or female connector configured to snap-fit couple to a corresponding male or female connector on a removable electrode.

While the embodiments of FIGS. 5A-5E show ECG sensing devices comprising three electrodes, it should be understood that the other numbers of ECG electrodes may be incorporated into the ECG sensing devices described herein.

In general, any of the techniques, components and/or subsystems described above may be use or combined with any of the other examples. For example, any of the ECG devices described herein may include any of the features mentioned above.

QTc prolongation, whether secondary to genetic and/or acquired risk factors, represents an independent risk factor for SCD and a predictor of both all-cause and cardiovascular mortality in a variety of clinical settings. Importantly, studies have demonstrated that ~1% of all individuals that receive an inpatient or outpatient 12-lead ECG have a QTc≥500 ms. It should be noted that this threshold, when met or exceeded, carries a ~2 to 4 fold increased risk of death and serves, at least in the short term (e.g., 30 days), as a powerful predictor of all-cause mortality that outperforms conventional co-morbidity indices. Although discussed herein with respect to a 500 ms threshold, any appropriate threshold (e.g., 450 ms, 475 ms) may be used to indicate QTc prolongation representing a heightened risk of cardiac disease related mortality. In addition, increases in QTc of a particular amount and over a particular time period may also be indicative of QTc prolongation representing a heightened risk of cardiac disease related mortality. For example, if a user's QT measures at 400 ms and subsequently at a later time (within a threshold time period) measures at 450 ms, this may indicate QTc prolongation even though 450 may be below the QTc threshold for an individual measurement (e.g., 500 ms).

Furthermore, in many circumstances, the development of a QTc≥500 ms is driven, at least in part, by the presence of a potentially lethal, but highly treatable genetic condition (i.e. congenital LQTS) and/or modifiable risk factors (e.g. electrolyte abnormalities, use of ≥1 QTc prolonging medication, or underlying QT agitating diseases). Therefore, in many circumstances, the identification of substantial QTc prolongation provides an important opportunity to i) identify vulnerable, at-risk hosts and ii) make potentially lifesaving change(s) (i.e. initiation of β-blockers, discontinuation of QTc-prolonging medications, or correction of hypokalemia and hypomagnesemia) needed to mitigate the risk of TdP and SCD.

However, due to the reliance on bulky 12-lead ECG systems and trained ECG technicians, the clinical settings in which the QTc can be monitored is limited largely to 'snap-shot' assessments in hospitals and outpatient clinics.

Thus, in some embodiments, the ECG sensing device 500 may be used to predict the QT interval of a user. As discussed herein, Machine learning (ML) is well suited for continuous monitoring of one or multiple criteria to identify anomalies or trends, big and small, in input data as compared to training examples used to train the model. ML models that may be used with embodiments described herein include by way of example and not limitation: Bayes, Markov, Gaussian processes, clustering algorithms, generative models, kernel and neural network algorithms. Some embodiments utilize a machine learning model based on a trained neural network (e.g., a trained recurrent neural network (RNN) or a trained convolution neural network (CNN)).

The ECG sensing device 500 may execute the module 510B in order to predict the QT interval as discussed herein. As described herein, the module 510B may comprise a deep neural network (DNN) for predicting QT interval however any appropriate ML model may be used. A user may position the ECG sensing device 500 in any appropriate manner described herein (e.g., in response to receiving instructions as discussed in further detail herein), and perform an ECG using the ECG sensing device 500. The processing device 505 may process the recorded ECG signals with an average beat algorithm and the input to the DNN may be the average beat in the form of a 2×450 length signal in millivolts. The average beat signal may first be clamped via a hyperbolic tangent function before going through an initial convolutional layer (e.g., 2D convolution, leaky rectified linear unit, max pooling) before being processed by three separate passthrough stages (two separate 2D convolutional, leaky rectified linear unit, max pooling, etc.), with the passthrough input added (via a trainable parameter) and dropout applied before downsampling, pooling, and convolution. After the final passthrough, the signal is sent through two separate feed-forward network layers outputting a probability vector for the output class of a given QT value, whose expectation value is taken to as the predicted QT interval. The loss function for training is a sum of a cross entropy term of the probability vector and the target QT interval, and a root mean error squared QT interval average. It should be noted that the ML model may utilize (and be trained on) any appropriate number and combination of leads. In some embodiments, the ML model may be trained to predict the QT interval based on a combination of leads I, II, or III and any appropriate v lead. For example, the ML model may be trained based on lead I and v5, lead II and v5, or lead III and v5 (or any other appropriate v lead).

The DNN may be trained using annotated standard 12-lead ECG data of a variety of patients taken in the same position in which the user was in when the ECG is taken. In some embodiments, the ECG signals may be preprocessed before training. For example, a bandpass filter may be applied to simulate the ambulatory bandwidth (0.1-40 Hz) of the ECG sensing device 500 and any appropriate filtering algorithm (e.g., Alivecor™'s FDA-cleared enhanced filtering algorithm) may be applied before processing the resulting 12-lead ECGs with an average beat algorithm for leads I and II. The source ECGs comprising the training data may be bucketed based on QT interval and randomly selecting ECGs within randomly selected buckets. Because the ECG signal received from the user may include leads that were generated using e.g., a separate lead conversion ML algorithm (e.g., via module 510A), in some embodiments, the DNN may be further adapted using additional training data including synthesized leads.

All of the devices described herein are suitable for use in various systems, which may include one or more servers, one or more sensors, an electronic data communication networks, as well as other ECG sensing devices. In some embodiments, a plurality of ECG sensing devices as described herein transmit ECG data to one or more remote servers through an electronic data communication network. In some embodiments, the ECG data is analyzed using the one or more remote servers. In some embodiments, arrhythmia detection is carried out using a remote server that analyzes received ECG data.

All of the devices and systems described herein may also include one or more software modules. In some embodiments, software comprises an application that is configured to run on a mobile computing device such as, for example, a smartphone, a smartwatch, or a tablet computer. The software receives and processes ECG data received from an ECG sensing device. The software identifies separate leads within the transmitted data, based on for example, which electrodes the ECG data originated from. For example, the software may be able to identify a lead I based on the signal originating from two electrodes that measure an electric potential difference between the right and left upper extremities. Once an ECG is identified, the software may further be configured to display a single or multi-lead ECG on a display screen of a mobile computing device. The software may be configured to display six leads I, II, III, aVR, aVL, and aVF simultaneously on a display screen. The software may be configured to display one or more of the six leads I, II, III, aVR, aVL, and aVF on a display screen at once, wherein a user is able to manually toggle screens to see a different lead or leads on different toggled screens.

The software modules described herein comprise computer readable and executable code. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

In some embodiments, two or more sensed leads that are not simultaneously sensed are time aligned to generate a time aligned ECG tracing displaying two or more leads in a time aligned format such as in a traditional standard twelve lead ECG tracing. In some embodiments of the ECG sensing device described herein, one or more ECG sensing electrodes are not simultaneously positioned on the skin of the individual whose ECG is sensed (i.e. some leads may be sequentially sensed). For example, the limb leads (I, II, III, aVR, aVL, and aVF) are simultaneously sensed while one or more of the precordial leads are sensed separately from the limb leads. As such, in these embodiments, the six limb leads are not automatically time aligned with the individually and separately sensed precordial leads and a further process is carried out by a software application to time align one or more of the limb leads with one or more of the precordial leads. In some embodiments, one or more of the six precordial leads are individually sensed so that the individually sensed precordial leads are time aligned by a software application with the six limb leads as well as with the other precordial leads. In some embodiments, a software application described herein aligns two or more sensed precordial leads with one another and separately time aligns six sensed limb leads so that two sets of six leads are respectively time aligned (i.e. six time aligned precordial leads and six separately time aligned limb leads). In some embodiments, the software described herein aligns two or more sensed precordial leads with one another as well as with sensed limb leads so that all twelve sensed leads are time aligned.

In some embodiments, one or more average or median waveforms are generated for a first and a second lead so that waveforms corresponding to different heartbeats are time aligned. That is, in some embodiments wherein one or more leads are not sensed concurrently, an average or median waveform is generated for one or more of these leads and the averaged or median waveforms are time-aligned so that the P, QRS, and T waveforms/complexes are aligned vertically along the X-axis.

The memory 510 may include a time alignment software module (not shown) which can perform time alignment of the P, QRS, and T waveforms/complexes of each lead sensed by the ECG sensing device 500 so that the sensed ECG leads are aligned when displayed as are the waveforms in a traditional ECG tracing. In some embodiments of the ECG sensing device, the ECG sensing device comprises a software application configured to time align two or more sensed ECG leads. In some embodiments of the ECG sensing device, a software application configured to time align two or more sensed ECG leads is a component of a system that receives data from an ECG sensing device.

When first and second electrodes of the ECG sensing device described herein are contacted by the right and left upper extremities of the user at the same time that a third electrode of the device contacts any one of the six precordial lead positions, a lead I is sensed simultaneously along with a sensed precordial lead. That is, lead I is equal to a voltage sensed at the left upper extremity minus a voltage sensed at the right upper extremity, so when left upper extremity, right upper extremity, and chest are all respectively contacted by an electrode of the ECG sensing device described herein, a lead I is sensed in addition to a precordial lead. Therefore, when all six precordial leads are sensed sequentially, six respectively corresponding "precordial lead I recordings" are also generated: V1-lead I, V2-lead I, V3-lead I, V4-lead I, V5-lead I, and V6-lead I. Each of these six precordial lead I recordings is used to time align each of the precordial leads to the limb leads and thus time aligns precordial leads.

In some embodiments, the time alignment software module aligns the precordial leads V1, V2, V3, V4, V5, and V6 by taking advantage of there being precordial lead I recordings sensed simultaneously with each of the V1, V2, V3, V4, V5, and V6 waveforms. That is, the precordial lead I recordings V1-lead I, V2-lead I, V3-lead I, V4-lead I, V5-lead I, and V6-lead I are each respectively time aligned with a precordial lead recording with which they are simultaneously sensed. Each of the precordial lead I recordings is time aligned with the lead I that is sensed along with the limb leads, by, for example, moving the precordial lead I recording a certain distance along the Y-axis, and because each of the precordial lead I recordings is time aligned with a precordial lead, each of the respective precordial leads V1, V2, V3, V4, V5, and V6 will also be time aligned when moved the same distance along the Y-axis as their co-sensed precordial lead I recording. For example, "V1-lead I" is a lead I recording that is time aligned with V1. "V1-lead I" is not the same as "lead I," which is the lead I recorded simultaneously sensed with the other five limb leads using the ECG sensing device described herein. "V1-lead I" is also not necessarily time aligned with "lead I" as these two different lead I recordings are not typically sensed simultaneously using the ECG sensing device described herein. Because, however, "V1-lead I" and "lead I" are both lead I recordings, they can be time aligned in a fairly straightforward manner as they would both be expected, when averaged, to have very similar (if not identical) morphology and timing between waveforms. For example, if the peak of the R wave of an averaged "lead I" occurs at 1 second, and the peak of the R wave of an averaged "V1-lead I" occurs at 1.5 seconds, the averaged "V1-lead I" will be re-positioned or shifted 0.5 seconds along the Y-axis so that the peak of its R wave occurs at 1 second as it does in in the averaged "lead I." Because V1 is time aligned with V1-lead I, it too must be shifted 0.5 seconds along the Y-axis in order to time align it with the averaged "lead I." When V1 is time aligned with "lead I," it will also be time aligned with the other five limb leads that are already time aligned with "lead I." A similar alignment occurs with V2, V3, V4, V5, and V6 by respectively aligning V2-lead I, V3-lead I, V4-lead I, V5-lead I, and V6-lead I with "lead I."

Figure 6:
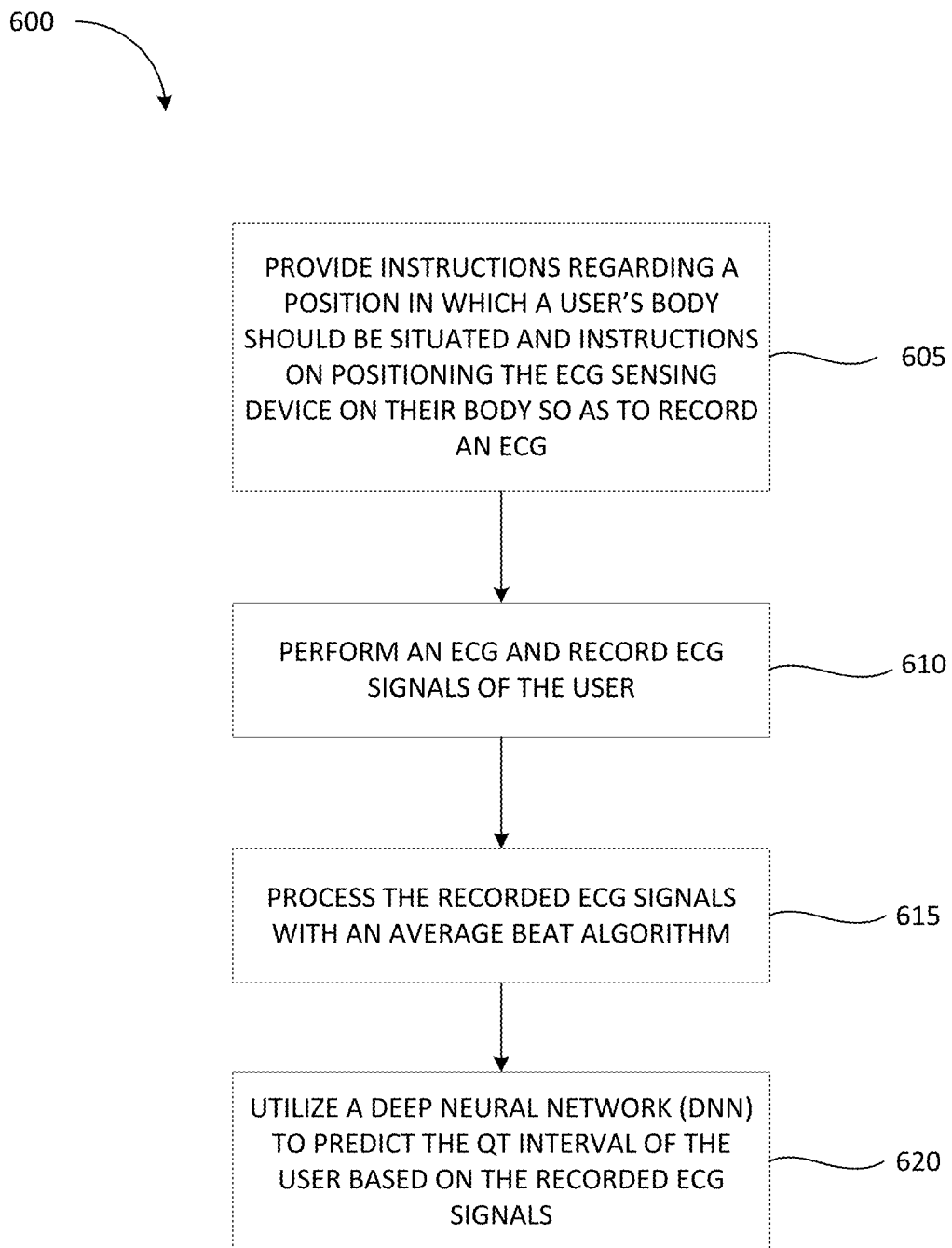
FIG. 6 is a flow diagram of a method for predicting a QT interval, in accordance with some embodiments of the present disclosure.

FIG. 6 is a flow diagram of a method 600 of predicting a QT interval, in accordance with some embodiments of the present disclosure. Method 600 may be performed by processing logic that may comprise hardware (e.g., circuitry, dedicated logic, programmable logic, a processor, a processing device, a central processing unit (CPU), a system-on-chip (SoC), etc.), software (e.g., instructions running/executing on a processing device), firmware (e.g., microcode), or a combination thereof. In some embodiments, the method 600 may be performed by ECG sensing device 500 (via processing device 505) as illustrated in FIG. 5A.

At block 605, the ECG sensing device 500 may provide to the user instructions (in some embodiments, computing device 550 may provide these instructions) regarding a position in which their body should be situated and instructions to position the ECG sensing device 500 on their body so as to record an ECG. At block 610, the processing device 505 may perform an ECG and acquire ECG signals of the user. At block 615, the processing device 505 may process the recorded ECG signals with an average beat algorithm and at block 620 the processing device 505 may execute module 510B in order to predict the QT interval of the user. As described herein, the module 510B may comprise a deep neural network (DNN) for predicting QT interval however any appropriate ML model may be used. The input to the DNN may be the average beat in the form of an e.g., 2×450 length signal in millivolts. The average beat signal may first be clamped via a hyperbolic tangent function before going through an initial convolutional layer (e.g., 2D convolution, leaky rectified linear unit, max pooling) before being processed by three separate passthrough stages (two separate 2D convolutional, leaky rectified linear unit, max pooling, etc.), with the passthrough input added (via a trainable parameter) and dropout applied before downsampling, pooling, and convolution. After the final passthrough, the signal may be sent through two separate feed-forward network layers outputting a probability vector for the output class of a given QT value, whose expectation value is taken to as the predicted QT interval. The loss function for training is a sum of a cross entropy term of the probability vector and the target QT interval, and a root mean error squared QT interval average.

In some embodiments, one or more electrodes may be external to the mobile computing device. In such an embodiment, the one or more external electrodes are wirelessly or hardwire coupled to a mobile computing device. Non-limiting examples of wireless connections may comprise, for example, a WiFi connection between the one or more external electrodes and the device, a Bluetooth® connection between the one or more external electrodes and the device, a low power BlueTooth connection between the one or more external electrodes and the device, an NFC (near field communication) connection between the one or more external electrodes and the device, or a near field ultrasound communication connection between the one or more external electrodes and the device. It should be understood by those having knowledge in the art that other means of communicating wirelessly with a device are suitable for use with the systems, devices, and methods described herein.

Additionally, software incorporated with any of the systems, devices, methods described herein may be configured to analyze ECG data received from an ECG sensing device. Analysis may comprise generating a QRS axis and a T axis value using the six leads I, II, III, aVR, aVL, and aVF as described herein. Additionally, software incorporated with any of the systems, devices, methods described herein may determine a QRST angle by calculating the difference between the QRS axis and T axis as described herein. Analysis may further comprise a rhythm analysis which may comprise determining a heart rate variability, a QT interval, or a corrected QT interval.

Additionally, software incorporated with any of the systems, devices, methods described herein may be used to determine a diagnosis or abnormality associated with an ECG. For example, as described an axis deviation may be associated with the abnormality of right or left ventricular hypertrophy. For example, heart rate variability may be associated with the diagnosis of atrial fibrillation. For example, QT interval changes may indicate certain arrhythmias.

Any of the systems, devices, and methods described herein may also be combined with sensors that measure physiologic parameters. For example, and of the systems, devices, or methods described herein may be incorporated with a blood pressure sensor. For example, any of the systems, devices, or methods described herein may be incorporated with a photoplethysmogram (PPG) sensor. For example, any of the systems, devices, or methods described herein may be incorporated with a temperature sensor. For example, any of the systems, devices, or methods described herein may be incorporated with a pulse oximetry sensor. For example, any of the systems, devices, or methods described herein may be incorporated with an accelerometer. Those having skill in the art will understand that other sensors that monitor or detect physiologic parameters are suitable for use with the systems, devices, and methods described herein.

In some embodiments, sensed physiologic data is transmitted to a processer in any of the systems, devices, and methods described herein. Software that is combined with any the systems, devices, and methods described herein may use said physiologic data that is sensed in combination with a sensed ECG to perform an analysis. For example, blood pressure data may be combined with ECG data by said software to provide an analysis that determines the presence of a ventricular tachycardia, an immediately life threatening condition.

The systems, devices, and methods described herein may include either or both of transmitters and receivers for transmitting and receiving wireless signals.

In some embodiments, software described herein also causes the transmission of a signal to a server when an abnormal analysis result is determined. For example, an abnormal analysis result comprises an abnormal ECG. For example, an abnormal analysis result comprises an abnormal QRS axis. For example, an abnormal analysis result comprises an abnormal QRST angle. In some embodiments, an abnormal analysis result comprises an abnormal ECG. For example, an abnormal analysis result comprises an abnormal heart rate variability value. For example, an abnormal analysis result comprises an abnormal physiologic parameter value. The transmitted signal may comprise a signal to an emergency care provider. For example, if an immediately life threatening condition is determined such as, for example, a VT the software described herein may send an emergency signal to an emergency operator, emergency care providers (e.g. paramedics), or other third party monitors.

A six lead ECG may be displayed on said display screen, said six lead ECG comprising said lead I, said lead II, said lead III, said lead aVR, said lead aVL, and said lead aVF.

While preferred embodiments of the systems, devices, and methods described herein have been shown and described herein, it will be obvious to those skilled in the art that such embodiments are provided by way of example only. Numerous variations, changes, and substitutions will now occur to those skilled in the art without departing from the user matter described herein. It should be understood that various alternatives to the embodiments of the systems, devices, and methods described herein may be employed in practicing the systems, devices, and methods described herein. It is intended that the following claims define the scope of the invention and that methods and structures within the scope of these claims and their equivalents be covered thereby.

In one embodiment, the method and systems describe herein may be combined with methods and systems for guiding and/or correcting placement of electrodes on a patient. These methods may be particularly useful for guiding placement of electrodes for ECG measurements. In general, the systems, devices and methods contemplated herein process a picture of a patient to output electrode positions on the patient. Typically, this may include presenting an image of the patient (e.g., a modified version of the picture of the patient) showing the locations for the electrodes relative to the actual patient picture.

For example, a system or device for guiding electrode placement as described herein may include control logic for controlling a processor (e.g., microprocessor of a computing device such as a hand-held computing device) to receive a picture of a patient, to analyze the patient to determine the correct placement of the electrodes, and to output an image of the patient on which the correct predetermined electrode positions have been marked. In general, the control logic may be configured as software, hardware or firmware, and may control a general-purpose computing device (e.g., computer, tablet, or the like) or a mobile telecommunications device (smartphone, such as Iphone™ Android™, etc.) to accept or acquire the picture and output the image of the patient. The processing step may be performed remotely or locally. In general, the processing step may include comparing the picture of the patient to a database (e.g., an electrode placement database) of various body types and corresponding predetermined, conventional or standard positions for electrodes associated with each body type. The picture of the patient may also be normalized prior to comparing the picture the patient database by adjusting the size, and/or in some cases the aspect ratio, brightness, contrast, or other image features, of the picture to allow direct comparison with the database. Normalization may be performed using a marker included as a part of the picture. For example, the picture of the patient may be taken with a marker of known or knowable size on the patient, and the marker may be used as a normalization marker to normalize the picture before comparison with the database. Normalization may also be performed to even out the brightness, contrast, sharpness, or other imaging quality of the picture. The marker may be placed or applied directly onto the patient (e.g., the patient's torso), e.g., by adhesive, etc.)

Also described contemplated are methods performed by the devices and systems for guiding electrode placement, such as methods of guiding electrode placement on a patient.

For example, contemplated herein are methods for guiding proper placement of electrodes on a patient that include: comparing a picture of the patient to an electrode placement database to determine positioning of electrodes on the patient, wherein the electrode placement database comprises representations of a plurality of body types and predetermined electrode placement positions corresponding to each body type; and presenting an image of the patient showing positions for electrodes on the image of the patient.

These methods may be particularly adapted for guiding placement of ECG electrodes on a patient in a standard or conventional configuration on the patient. Thus, the database may be configured to include a plurality of body types with corresponding conventional/standard electrode placement positions for each body type in the database.

In some variations electrode positions may be determined and indicated for all of the electrodes (e.g., all 10 electrode positions used for a standard 12 electrode lead). However, in some variations on a subset of the electrode positions may be determined and/or displayed. For example, a method of guiding positioning of a standard/conventional 12-lead electrode placement may determine and show only the six electrode positions on the patient's chest. In some variations where other electrode positions may be determined relative to one or more key electrode positions, only the position of the key electrode(s) may be shown.

In general, any appropriate picture of the subject may be used. In some variations, the system, devices or methods may include taking or acquiring the picture. In some variations, the picture may be taken by the system or device performing the method (e.g., a smartphone or other hand-held computer device). The systems, devices and methods described herein may instruct a user how to take the picture of the patient, including positioning the patient (facing forward, standing, sitting, lying, etc.), approximately how far from the patient to take the picture, positioning a normalization marker on or near the patient, and the like. The picture may be received as a digital image. The picture may include an image of the patient, and particularly a region of the patient's body to which the electrodes are to be applied. For example, when applying ECG electrodes, the picture may include the patient's torso or chest. Additional regions of the patient's body may be included, such as the patient's head, legs, etc. The patient may be standing, seated or lying down. The region of the patient to which the electrodes will be applied is typically bare (e.g., a may be shirtless or at least partially shirtless, so that the skin can be visualized). As mentioned, in some variations a normalization marker may be included as part of the picture. For example, a reference marker may be placed on the patient; the reference/normalization marker typically has a known or standard size, such as a coin (e.g., a U.S. quarter, penny, etc.). In some variations the reference marker is provided, and may be a distinct shape or color. In some variations the marker is automatically recognized by the apparatus. For example, the marker may include a readable code (e.g. bar code, alphanumeric code, QR code, etc.); alternatively, the apparatus may identify the marker by color, shape, etc.

In variations in which the method, system or device guides the user through taking or acquiring the picture, the picture may be qualified by the system or device. Qualifying the picture may include checking the picture to confirm that it is suitable and can be analyzed (e.g., compared) to the database.

As used herein the phrases "user" and "patient" are intended broadly to include any subject on whom the methods, devices and systems may be used to help position electrodes. A patient may include an animal (in systems and devices specifically configured for use with that type of animal) or human, and may include healthy or non-healthy subjects. As used herein a "user" may be a person using the systems, methods and devices as described herein. In some variations the user is the same as the patient, as the systems, devices and methods described herein may be used by a patient to guide placement of electrodes on his or herself.

In some variations, comparing the picture to the electrode placement database may comprise determining the standard placement of electrodes for a 12-lead ECG on the patient.

In general, comparing the picture of the patient to the electrode placement database may include determining a match (e.g., the closest match) between the picture and one or more representative body types in the patient database. Once one or more closely matching representative body types have been identified, the electrode placement corresponding to the representative body types for the match(es) may be mapped to the picture of the patient. Where more than one match is identified, electrode placement may be determined from the standard electrodes placements corresponding to the multiple representative body matches by weighting, averaging, or other appropriate statistical method for finding a consensus standard among the closest matches, and mapping this standard electrode placement to the picture of the patient.

As described in greater detail below, an electrode placement database typically includes a plurality (e.g., >10, >100, >1000, >10,000, etc.) of representations of standard/conventional electrode placement for different bodies. A representation of a body type may include an image of a body (e.g., picture, portion of a picture, etc.) or information extracted from an image of a body including electrode placement specific for that body, where the electrode placement has been confirmed or verified as within the standard/conventional bounds. The various body types may include body types of different shapes and sizes (height, weight, morphology), gender (male/female), age (infant, child, adult, elderly), physical morphology (shoulder width, chest size, waist size, etc.), and the like. Each body type representation may be unique, although similar body types may be included, creating clusters of body types around more common body types. All of the body types in the database may be pre-normalized to allow comparison between the different representations. Multiple different electrode placement databases may be used. For example, separate databases may be used for different patient positions (lying, sitting, standing, etc.), or for different patient genders, ages, etc. Further, different electrode placement databases may be used for different standard/conventional electrode placements.

Thus, in addition to normalizing the picture before comparing it to an electrode placement database, the picture may be processed to prepare it for comparison with the database. In variations in which the comparison is made by extracting features from the picture and comparing these extracted features to the representations of body types in the database, the extraction of features may be performed on the picture before (or as part of) the comparison. For example, when comparing the picture of the patient to the electrode placement database includes determining anatomical landmarks from the picture and comparing the anatomical landmarks to the electrode placement database, anatomical landmarks may be extracted from the picture first. The picture may also be processed to remove patient-identifying features (e.g., all or part of the patients face, etc.) which may be relevant to protect patient privacy.

As mentioned above, the comparison of the picture with the database may comprises interpolating between the closest matches to the picture and two or more representative body types in the patient database.

In some variations, comparing the picture of the patient to the database comprises using pattern recognition to determine the closest match between the picture and a representative body type in the database. In some variations, comparing the picture of the patient to the electrode placement database comprises comparing the normalized picture of the patient to the electrode placement database.

The methods, devices and systems contemplated herein may also include presenting the image of the patient showing positions for electrodes on the image of the patient. Any appropriate image of the patient may be presented, including a modified version of the picture of the patient showing the positions of the electrodes determined by comparison with the database. In some variations, the image of the patient is digitally displayed (e.g., on the handheld computing device). And may be enlarged (zoom in/out) or manipulated so that the user can see where to place the electrodes. In some variations the image may include additional guidelines, including measurements (rulers, distances in inches, mm, etc.) relative to the patient, including patient landmarks, such as anatomical landmarks, and/or relative to other electrodes.

The presentation of the image of the patient showing the conventional/standard position of the electrodes may show all of the electrodes, or some of the electrodes. In some variations, the presentation of the image may include a series of images separately showing the patient with different electrode positions indicated, to better allow a user to step through the process of applying or repositioning the electrodes. In general, the presentation of the image of the patient may be visual (showing the image) and may also include textual (written/spoken) instructions for applying the electrodes. For example, in variations of the systems and methods described herein intended for use with a handheld computer device, such as a smartphone, the device may be controlled to step the user through both taking the patient's picture and positioning (or repositioning) the electrodes by looking at the screen of the smartphone.

In some variations, the methods, devices and systems described herein may be used to correct and/or verify the position of electrodes already present on a patient. For example, the user may take or receive a picture of a patient with ECG electrodes already on the chest. Comparing the picture of the patient to the electrode-placement database may also compare the position of the electrodes already on the patient with the determined standard/conventional positions. Thus, comparing the picture of the patient to an electrode placement database may comprise comparing a picture of the patient having one or more electrodes already placed on the patient's chest to the electrode placement database. The position of the one or more electrodes already placed on the patient's chest may then be verified either automatically (indicating when one or more is incurred) or passively by overlying the correct positions (indicated in some specific way, e.g., by a color) onto the picture of the patient to form the presented image. In some variations the image presented includes an image of the patient showing corrected positioning of electrodes on the image of the patient.

Also contemplated herein are methods for guiding placement of ECG electrodes that include: receiving a picture of a patient including the patient's chest; comparing the picture of the patient to an electrode placement database to determine positioning of electrodes on the patient, wherein the electrode placement database comprises representations of a plurality of body types and predetermined conventional ECG electrode placement positions corresponding to each body type; and presenting an image of the patient showing positions for conventional ECG electrode positions on the image of the patient. The method of claim 17, wherein comparing the picture of the patient to the electrode placement database includes determining the closest match between the picture and a representative body type in the electrode placement database.

As mentioned above, comparing the picture of the patient to the electrode placement database includes determining anatomical landmarks from the picture and comparing the anatomical landmarks to the electrode placement database. In some variations, comparing the picture of the patient to the database comprises using pattern recognition to determine the closest match between the picture and a representative body type in the electrode placement database.

In any of the variations described herein, the comparing of the patient picture with the electrode placement database may be performed remotely from the other steps. For example, a smartphone may be used (e.g., using an application downloaded to the phone) to acquire the picture of the patient, and to present the image of the patient showing the conventional positions of the electrodes; the comparison of the picture with the database may be performed remotely, using a remote server. Thus, the database may be maintained separately from the application on the smartphone (or other device). This may allow modification, updating, or otherwise amending the database and/or the mechanisms for comparing the picture of the patient to the database. The image generated may then be presented on a handheld computer device after it receives information (or the generated image) back from the remote database. Alternatively, in some variations all of the steps are performed on the local level (e.g., using the handheld computing device, such as a smartphone or tablet computer).

As mentioned above, the picture of the patient may include a normalization marker. Thus the step of receiving the picture of a patient may include receiving a picture of a patient includes a normalization marker. In some variations, the picture of the patient received may include electrodes on the patient's chest; the method, device or system may verify the placement of the electrodes already on the chest relative to conventional ECG electrode placement positions.

Also described herein are methods for determining the placement of ECG electrodes including: receiving a picture showing a patient including and a normalization marker; normalizing the picture using the normalization marker; comparing the normalized picture to an electrode placement database comprising representations of a plurality of body types and predetermined ECG electrode placement positions for each body type to determine positioning of electrodes on the patient; and presenting an image of the patient showing positions for ECG electrodes on the image of the patient.

A system or device may be configured to perform any or all of the steps described above for receiving a picture of a patient including the region of the patient to which electrodes are to be applied, analyzing the picture, and providing an image of the patient (or any other patient-specific map) showing the location(s) of one or more electrodes on the patient based on predetermined, conventional and/or standard electrode positions.

Although many of the examples described herein are specific to systems, devices and methods of placing ECG electrodes (e.g., of a device 500) according to standard or convention 12-lead ECG electrode placement, these systems, devices and methods may be used (or adapted for use) with any predetermined, conventional and/or standard electrode positioning system, including electrodes for electroencephalograms (EEG), electromyogram (EMG), galvanic skin reflex (GSR), electrooculogram (EOG), bioimpedance (BI), etc. For example, the electrode placement database may include a variety of body types and corresponding predetermined, conventional and/or standard electrode positions for each of the body types for EEG, EMG, GSR, EOG, BI, etc. In some variations, the different electrode placement regimes (different conventional and/or standard electrode placement) may be linked in the database to each body type, and a user may select which placement regime to display. In other variations, more than one placement regime may be shown, either sequentially or simultaneously, for the same patient. For example, for ECG electrode placement, the electrode placement can correspond to 3-lead, 5-lead, and 12-lead ECGs.

A system for guiding electrode placement may generally include control logic, which may be executed as software, hardware, or firmware (or combinations thereof) that receive the picture of the patient, determine conventional and/or standard electrode placement for that patient using an electrode placement database, and output a map or image of the patient showing where on the patient the electrodes should be positioned. The system may also be configured to guide or walk the user through the process of taking the picture of the patient and/or positioning the electrodes on the patient. In some variations, the system is configured to guide the user by audible instructions, written instructions and/or visual instructions. The system may be configured to work from (e.g., control) a handheld computing device, including a smartphone (e.g., iPHONE, ANDROID, etc.) to receive (and in some cases take) the picture of the patient and output the image of the patient with the determined electrode position(s) marked. For example, the system may be configured as an application for a smartphone that is downloadable onto the smartphone.

Any of the systems described herein may be dedicated systems that come pre-configured to receive a patient picture and output an image of the patient showing electrode placement positions, and do not require downloading of an application (e.g., software) onto a separate device. For example, a system may include a camera for taking a picture of the patient, control logic for receiving the picture, controlling analysis of the picture to determine electrode placement using an electrode placement database, and outputting a map or image of the patient showing the location of one or more electrodes according to a conventional and/or standard electrode positioning regime. The system may include all or a portion of the electrode placement database, or the system may communicate with a remote electrode placement database. Further, the system may include a comparison unit, which may include comparison logic for comparing the picture of the patient with the body types in the electrode placement database in order to find one or more close matches between the patient and the body types in the database, from which the predetermined conventional and/or standard electrode positions can be extrapolated to the patient picture.

The system may also be configured to use (and may include as part of the system) a normalization marker that is included in the picture of the patient. A normalization marker is typically a distinct marker that the systems/devices described herein may distinguish in the picture, and which may be used to provide scale and/or orientation for reference in the picture. For example, the normalization marker may be a sticker that can be attached to the skin of the patient; the sticker may be brightly colored, and may have a known size (e.g., an orange circle of one inch diameter). The system/device can therefore distinguish this sizing marker in the picture, and can normalize the picture using the normalization marker. In some variations the normalization marker may also provide a reference position which the system may use in providing instructions for placement of the electrode(s). In some variation more than one sizing marker may be used. A normalization marker may be a common object of known dimension, such as a coin. The user may indicate in the system/device what the normalization marker (e.g., from a menu of possible normalization markers).

As mentioned, the image of the patient showing positioning of electrodes can be presented to the user on a handheld computer device. For example, the handheld computer device can be a mobile phone, smartphone, tablet computer, or camera with network connectivity.

Figure 7:
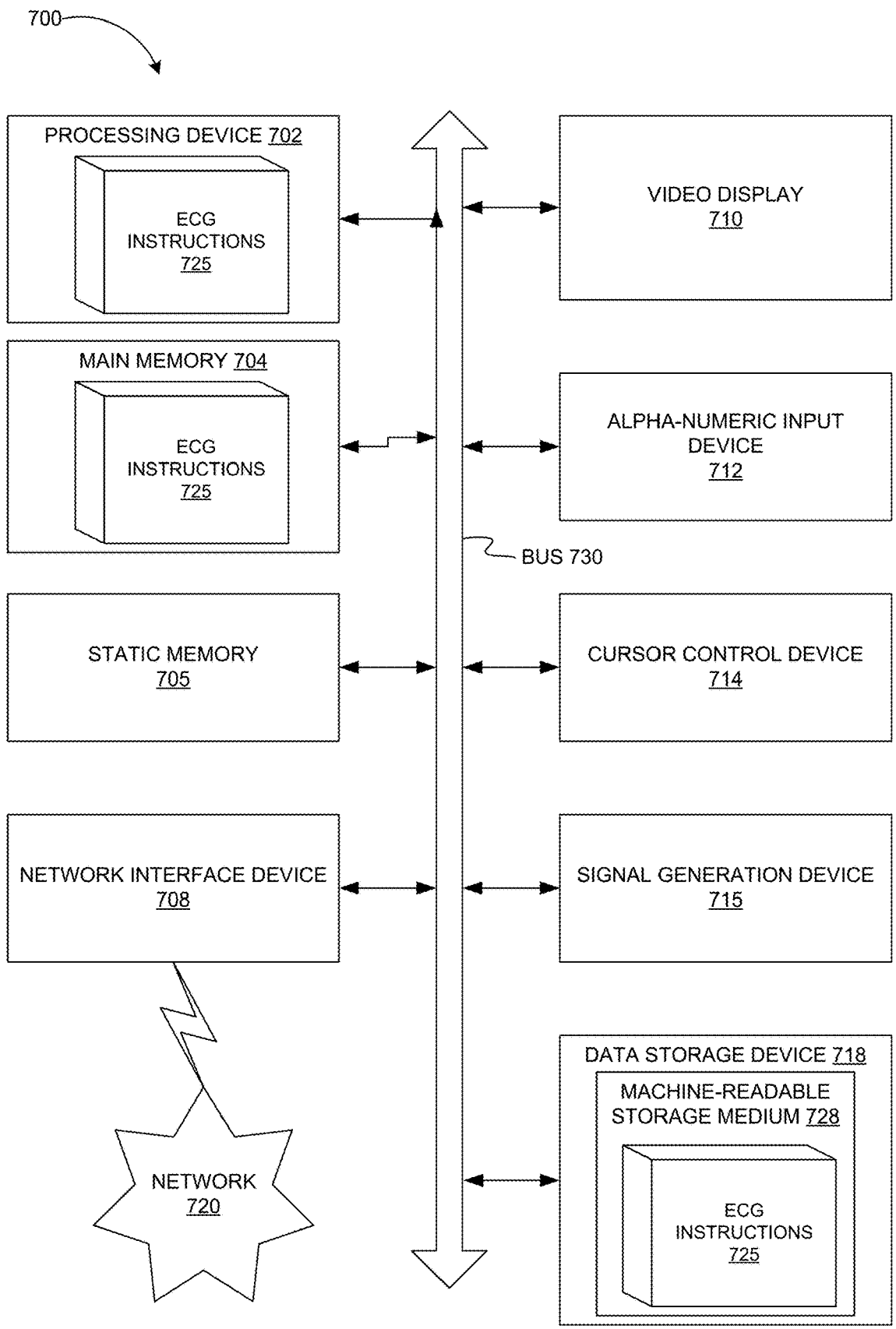
FIG. 7 is a block diagram of an example computing device that may perform one or more of the operations described herein, in accordance with some embodiments of the present disclosure.

FIG. 7 is a block diagram of an example computing device 700 that may perform one or more of the operations described herein, in accordance with some embodiments. In some embodiments, computing device 700 may represent internal hardware of ECG device 500. Computing device 700 may be connected to other computing devices in a LAN, an intranet, an extranet, and/or the Internet. The computing device may operate in the capacity of a server machine in client-server network environment or in the capacity of a client in a peer-to-peer network environment. The computing device may be provided by a personal computer (PC), a set-top box (STB), a server, a network router, switch or bridge, or any machine capable of executing a set of instructions (sequential or otherwise) that specify actions to be taken by that machine. Further, while only a single computing device is illustrated, the term "computing device" shall also be taken to include any collection of computing devices that individually or jointly execute a set (or multiple sets) of instructions to perform the methods discussed herein.

The example computing device 700 may include a processing device (e.g., a general purpose processor, a PLD, etc.) 702, a main memory 704 (e.g., synchronous dynamic random access memory (DRAM), read-only memory (ROM)), a static memory 706 (e.g., flash memory and a data storage device 718), which may communicate with each other via a bus 730.

Processing device 702 may be provided by one or more general-purpose processing devices such as a microprocessor, central processing unit, or the like. In an illustrative example, processing device 702 may comprise a complex instruction set computing (CISC) microprocessor, reduced instruction set computing (RISC) microprocessor, very long instruction word (VLIW) microprocessor, or a processor implementing other instruction sets or processors implementing a combination of instruction sets. Processing device 702 may also comprise one or more special-purpose processing devices such as an application specific integrated circuit (ASIC), a field programmable gate array (FPGA), a digital signal processor (DSP), network processor, or the like. The processing device 702 may be configured to execute the operations described herein, in accordance with one or more aspects of the present disclosure, for performing the operations and steps discussed herein.

Computing device 700 may further include a network interface device 708 which may communicate with a network 720. The computing device 700 also may include a video display unit 710 (e.g., a liquid crystal display (LCD) or a cathode ray tube (CRT)), an alphanumeric input device 712 (e.g., a keyboard), a cursor control device 714 (e.g., a mouse) and an acoustic signal generation device 716 (e.g., a speaker). In one embodiment, video display unit 710, alphanumeric input device 712, and cursor control device 714 may be combined into a single component or device (e.g., an LCD touch screen).

Data storage device 718 may include a computer-readable storage medium 728 on which may be stored one or more sets of ECG instructions 726, e.g., instructions for carrying out the operations described herein, in accordance with one or more aspects of the present disclosure. ECG instructions 726 may also reside, completely or at least partially, within main memory 704 and/or within processing device 702 during execution thereof by computing device 700, main memory 704 and processing device 702 also constituting computer-readable media. The instructions 726 may further be transmitted or received over a network 720 via network interface device 708.

While computer-readable storage medium 728 is shown in an illustrative example to be a single medium, the term "computer-readable storage medium" should be taken to include a single medium or multiple media (e.g., a centralized or distributed database and/or associated caches and servers) that store the one or more sets of instructions. The term "computer-readable storage medium" shall also be taken to include any medium that is capable of storing, encoding or carrying a set of instructions for execution by the machine and that cause the machine to perform the methods described herein. The term "computer-readable storage medium" shall accordingly be taken to include, but not be limited to, solid-state memories, optical media and magnetic media.

The methods and illustrative examples described herein are not inherently related to any particular computer or other apparatus. Various general purpose systems may be used in accordance with the teachings described herein, or it may prove convenient to construct more specialized apparatus to perform the required method steps. The required structure for a variety of these systems will appear as set forth in the description above.

The above description is intended to be illustrative, and not restrictive. Although the present disclosure has been described with references to specific illustrative examples, it will be recognized that the present disclosure is not limited to the examples described. The scope of the disclosure should be determined with reference to the following claims, along with the full scope of equivalents to which the claims are entitled.

As used herein, the singular forms "a", "an" and "the" are intended to include the plural forms as well, unless the context clearly indicates otherwise. It will be further understood that the terms "comprises", "comprising", "includes", and/or "including", when used herein, specify the presence of stated features, integers, steps, operations, elements, and/or components, but do not preclude the presence or addition of one or more other features, integers, steps, operations, elements, components, and/or groups thereof.

Therefore, the terminology used herein is for the purpose of describing particular embodiments only and is not intended to be limiting.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Although the method operations were described in a specific order, it should be understood that other operations may be performed in between described operations, described operations may be adjusted so that they occur at slightly different times or the described operations may be distributed in a system which allows the occurrence of the processing operations at various intervals associated with the processing.

Various units, circuits, or other components may be described or claimed as "configured to" or "configurable to" perform a task or tasks. In such contexts, the phrase "configured to" or "configurable to" is used to connote structure by indicating that the units/circuits/components include structure (e.g., circuitry) that performs the task or tasks during operation. As such, the unit/circuit/component can be said to be configured to perform the task, or configurable to perform the task, even when the specified unit/circuit/component is not currently operational (e.g., is not on). The units/circuits/components used with the "configured to" or "configurable to" language include hardware—for example, circuits, memory storing program instructions executable to implement the operation, etc. Reciting that a unit/circuit/component is "configured to" perform one or more tasks, or is "configurable to" perform one or more tasks, is expressly intended not to invoke 35 U.S.C. 112, sixth paragraph, for that unit/circuit/component. Additionally, "configured to" or "configurable to" can include generic structure (e.g., generic circuitry) that is manipulated by software and/or firmware (e.g., an FPGA or a general-purpose processor executing software) to operate in manner that is capable of performing the task(s) at issue. "Configured to" may also include adapting a manufacturing process (e.g., a semiconductor fabrication facility) to fabricate devices (e.g., integrated circuits) that are adapted to implement or perform one or more tasks. "Configurable to" is expressly intended not to apply to blank media, an unprogrammed processor or unprogrammed generic computer, or an unprogrammed programmable logic device, programmable gate array, or other unprogrammed device, unless accompanied by programmed media that confers the ability to the unprogrammed device to be configured to perform the disclosed function(s).

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the embodiments and its practical applications, to thereby enable others skilled in the art to best utilize the embodiments and various modifications as may be suited to the particular use contemplated. Accordingly, the present embodiments are to be considered as illustrative and not restrictive, and the invention is not to be limited to the details given herein, but may be modified within the scope and equivalents of the appended claims.

What is claimed is:

1. A mobile electrocardiogram (ECG) sensor comprising:
an electrode assembly comprising electrodes, wherein the electrode assembly is configured to sense heart-related signals when in contact with a body of a user, and produce electrical signals representing the sensed heart-related signals;
a processing device, operatively coupled to the electrode assembly, the processing device to:
provide a training data set comprising a plurality of electrocardiogram (ECG) measurements and a corresponding QT interval label for each of the plurality of ECG measurements;
train a machine learning (ML) model by:
analyzing, using the ML model, each of the plurality of ECG measurements to generate an output;
comparing each of the plurality of outputs to a corresponding QT interval label to generate an error that is based on a cross entropy term of the output and the corresponding QT interval label; and
updating the ML model based on the error generated for each of the plurality of outputs;
analyze the sensed heart-related signals using the machine learning model to predict a twelve-lead QT interval (QTc) value based on the sensed heart-related signals, wherein the sensed heart-related signals comprise less than twelve leads; and
analyze, using the machine learning model, the predicted QTc value to determine whether a health anomaly is present; and
a housing containing the electrode assembly and the processing device.

2. The mobile ECG sensor of claim 1, wherein the plurality of electrocardiogram (ECG) measurements comprise twelve-lead ECG measurements from a plurality of users and the ML model is trained to predict the twelve-lead QTc value for a single user.

3. The mobile ECG sensor of claim 1, wherein the plurality of electrocardiogram (ECG) measurements comprise twelve-lead ECG measurements from a single user and the ML model is trained to predict the twelve-lead QTc value for the single user.

4. The mobile ECG sensor of claim 1, wherein the ML model is a deep neural network machine learning module.

5. The mobile ECG sensor of claim 1, wherein the sensed heart-related signals comprise Lead I and Lead II signals.

6. The mobile ECG sensor of claim 1, wherein the health anomaly is determined to be present when QTc prolongation is detected.

7. The mobile ECG sensor of claim 1, wherein the processing device is further configured to send a notification to a client device in response to the health anomaly being present.

8. The mobile ECG sensor of claim 6, wherein QTc prolongation corresponds to an increase in QTc that is above a threshold amount and within a threshold amount of time.

9. The mobile ECG sensor of claim 1, wherein the processing device determines that the health anomaly is present when QTc prolongation is detected from the predicted QTc value.

10. The mobile ECG sensor of claim 1, wherein the processing device is further to send a notification to a client device in response to determining that the health anomaly is present.

11. A mobile electrocardiogram (ECG) system comprising:
- an electrode assembly comprising electrodes, wherein the electrode assembly is configured to sense heart-related signals when in contact with a body of a user, and produce electrical signals representing the sensed heart-related signals;
- a processing device, operatively coupled to the electrode assembly, the processing device to:
  - provide a training data set comprising a plurality of electrocardiogram (ECG) measurements and a corresponding QT interval label for each of the plurality of ECG measurements;
  - train a machine learning (ML) model by:
  - analyzing, using the ML model, each of the plurality of ECG measurements to generate an output;
  - comparing each of the plurality of outputs to a corresponding QT interval label to generate an error that is based on a cross entropy term of the output and the corresponding QT interval label; and
  - updating the ML model based on the error generated for each of the plurality of outputs;
  - analyze the sensed heart-related signals using the ML model to predict a twelve-lead QT interval (QTc) value based on the sensed heart-related signals, wherein the sensed heart-related signals comprise less than twelve leads; and
  - analyze, using the ML model, the predicted QTc value to determine whether a health anomaly is present;
- a display operably connected to the processing device; and
- a memory comprising instructions to cause the processing device to process the sensed heart-related signals and display the heart-related signals and the predicted QTc value on the display.

12. The mobile ECG system of claim 11, wherein the ML model is trained on twelve-lead QTc interval data from a plurality of users to predict the twelve-lead QTc value for a single user.

13. The mobile ECG system of claim 11, wherein the ML model is trained on twelve-lead QTc interval data from a single user to predict the twelve-lead QTc value for the single user.

14. The mobile ECG system of claim 11, wherein the ML model is a deep neural network machine learning module.

15. The mobile ECG system of claim 11, wherein the sensed heart-related signals comprise Lead I and Lead II signals.

16. The mobile ECG sensor of claim 11, wherein the health anomaly is determined to be present when QTc prolongation is detected.

17. The mobile ECG sensor of claim 11, wherein the processing device is further configured to send a notification to a client device in response to the health anomaly being present.

18. The mobile ECG system of claim 16, wherein QTc prolongation corresponds to an increase in QTc that is above a threshold amount and within a threshold amount of time.

19. The mobile ECG system of claim 11, wherein the processing device determines that the health anomaly is present when QTc prolongation is detected from the predicted QTc value.

20. The mobile ECG sensor of claim 11, wherein the processing device is further to send a notification to a client device in response to determining that the health anomaly is present.

21. A method, comprising:
- providing a training data set comprising a plurality of electrocardiogram (ECG) measurements and a corresponding QT interval label for each of the plurality of ECG measurements;
- training a machine learning (ML) model by:
  - analyzing, using the ML model, each of the plurality of ECG measurements to generate an output;
  - comparing each of the plurality of outputs to a corresponding QT interval label to generate an error that is based on a cross entropy term of the output and the corresponding QT interval label; and
  - updating the ML model based on the error generated for each of the plurality of outputs;
- receiving, from an electrode assembly comprising electrodes, heart-related signals sensed by the electrode assembly from a body of a user;
- generating electrical signals representing the sensed heart-related signals;
- analyzing, by a processing device, the heart-related signals using the ML model to predict a twelve-lead QT interval (QTc) value based on the sensed heart-related signals, wherein the sensed heart-related signals comprise less than twelve leads; and
- analyzing, by the processing device, the predicted QTc value using the ML model to determine whether a health anomaly is present.

22. The method of claim 21, wherein the plurality of electrocardiogram (ECG) measurements comprise twelve-lead ECG measurements from a plurality of users to predict the twelve-lead QTc value for a single user.

23. The method of claim 21, further comprising determining the health anomaly to be present when QTc prolongation is detected from the predicted QTc value.

24. The method of claim 21, further comprising sending a notification to a client device in response to the health anomaly being present.

25. The method of claim 23, wherein QTc prolongation corresponds to an increase in QTc that is above a threshold amount and within a threshold amount of time.

* * * * *